(12) United States Patent
Leven

(10) Patent No.: US 9,993,637 B2
(45) Date of Patent: Jun. 12, 2018

(54) ELECTRICAL STIMULATION LEAD WITH JUNCTION AND METHODS OF MAKING AND USING

(71) Applicant: BOSTON SCIENTIFIC NEUROMODULATION CORPORATION, Valencia, CA (US)

(72) Inventor: Jacob B. Leven, Huntington Beach, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1115 days.

(21) Appl. No.: 13/972,135

(22) Filed: Aug. 21, 2013

(65) Prior Publication Data

US 2014/0058488 A1 Feb. 27, 2014

Related U.S. Application Data

(60) Provisional application No. 61/693,680, filed on Aug. 27, 2012.

(51) Int. Cl.
*A61N 1/00* (2006.01)
*A61N 1/05* (2006.01)

(52) U.S. Cl.
CPC .............. *A61N 1/05* (2013.01); *A61N 1/0551* (2013.01); *Y10T 29/49117* (2015.01)

(58) Field of Classification Search
CPC ................................ A61N 1/05; A61N 1/0551
USPC .................................................. 607/116–117
See application file for complete search history.

(56) References Cited

U.S. PATENT DOCUMENTS

| | | |
|---|---|---|
| 6,181,969 B1 | 1/2001 | Gord |
| 6,516,227 B1 | 2/2003 | Meadows et al. |
| 6,609,029 B1 | 8/2003 | Mann et al. |
| 6,609,032 B1 | 8/2003 | Woods et al. |
| 6,741,892 B1 | 5/2004 | Meadows et al. |
| 7,031,774 B1 | 4/2006 | Doan et al. |
| 7,244,150 B1 | 7/2007 | Brase et al. |
| 7,672,734 B2 | 3/2010 | Anderson et al. |
| 7,761,165 B1 | 7/2010 | He et al. |
| 7,949,395 B2 | 5/2011 | Kuzma |

(Continued)

OTHER PUBLICATIONS

International Search Report and Written Opinion for PCT/US2013/055944 dated Feb. 17, 2014.

*Primary Examiner* — Nicole F Johnson
(74) *Attorney, Agent, or Firm* — Lowe Graham Jones PLLC; Bruce E. Black

(57) ABSTRACT

A lead arrangement includes a plurality of proximal leads, a distal lead, and a junction electrically and mechanically coupling the plurality of proximal leads to the at least one distal lead. Each proximal lead has a proximal end and a distal end and includes conductive contacts disposed along the proximal end and conductive wires coupled to the conductive contacts and extending to the distal end of the proximal lead. Each distal lead has a proximal end and a distal end and includes electrodes disposed along the distal end and conductive wires coupled to the electrodes and extending to the proximal end of the distal lead. The junction includes conductive tabs and a non-conductive material encapsulating the conductive tabs. The conductive wires of the at least one distal lead and the conductive wires of the plurality of proximal leads are attached to the conductive tabs of the junction.

20 Claims, 28 Drawing Sheets

(56) References Cited

U.S. PATENT DOCUMENTS

| | | |
|---|---|---|
| 7,974,706 B2 | 7/2011 | Moffitt et al. |
| 8,175,710 B2 | 5/2012 | He |
| 8,224,460 B2 | 7/2012 | Brase |
| 8,364,278 B2 | 1/2013 | Pianca et al. |
| 2003/0077935 A1 | 4/2003 | Stein et al. |
| 2005/0049609 A1 | 3/2005 | Gunderson et al. |
| 2005/0272280 A1* | 12/2005 | Osypka ............ A61N 1/056 439/71 |
| 2007/0150036 A1 | 6/2007 | Anderson |
| 2010/0057176 A1* | 3/2010 | Barker ............ A61N 1/0551 607/117 |
| 2010/0256693 A1 | 10/2010 | McDonald et al. |
| 2011/0253415 A1 | 10/2011 | Muschiatti et al. |
| 2012/0029596 A1 | 2/2012 | Barker |

\* cited by examiner

SECTION A-A'

US 9,993,637 B2

ELECTRICAL STIMULATION LEAD WITH JUNCTION AND METHODS OF MAKING AND USING

CROSS-REFERENCE TO RELATED APPLICATIONS

This application claims the benefit under 35 U.S.C. § 119(e) of U.S. Provisional Patent Application Ser. No. 61/693,680 filed on Aug. 27, 2012, which is incorporated herein by reference.

FIELD OF THE INVENTION

The present invention is directed to the area of implantable electrical stimulation systems and leads and associated methods of making and using such systems and leads. More particularly, the present invention is directed to leads with connection junctions and methods of making and using such leads.

BACKGROUND

Implantable electrical stimulation systems have proven therapeutic in a variety of diseases and disorders. For example, implantable electrical stimulation systems may be implanted in the spinal cord to treat chronic pain syndromes and in the brain to treat refractory chronic pain syndromes, movement disorders, and epilepsy. Peripheral nerve stimulation systems may be used to treat chronic pain syndrome and incontinence. In some cases, paralyzed extremities in spinal cord injury patients may be treated using functional electrical stimulation. Moreover, electrical stimulation systems can be implanted subcutaneously to stimulate subcutaneous tissue including subcutaneous nerves such as the occipital nerve.

An electrical stimulation system can include a control module (with a pulse generator), one or more leads, and an array of stimulator electrodes mounted on the lead. The stimulator electrodes are placed in contact with or near the nerves, muscles, or other tissue to be stimulated. The pulse generator in the control module generates electrical pulses that are delivered through the electrodes to body tissue.

Conventional medical leads for use with pulse generators, such as neurostimulators, pacemakers, defibrillators or implantable cardioverter defibrillators ("ICD"), have proximal ends arranged for mechanical and electrical connection to the control module.

BRIEF SUMMARY

One embodiment is a lead arrangement including a plurality of proximal leads, a distal lead, and a junction electrically and mechanically coupling the plurality of proximal leads to the at least one distal lead. Each proximal lead has a proximal end and a distal end and includes conductive contacts disposed along the proximal end and conductive wires coupled to the conductive contacts and extending to the distal end of the proximal lead. Each distal lead has a proximal end and a distal end and includes electrodes disposed along the distal end and conductive wires coupled to the electrodes and extending to the proximal end of the distal lead. The junction includes conductive tabs and a non-conductive material encapsulating the conductive tabs. The conductive wires of the at least one distal lead and the conductive wires of the plurality of proximal leads are attached to the conductive tabs of the junction.

Another embodiment is a method of making a coupled lead arrangement. The method includes providing a pre junction element with tabs extending from at least one runner; attaching exposed ends of a plurality of conductive wires from a plurality of proximal leads and from at least one distal lead to the tabs of the pre junction element to form a connected pre junction element. For each of the tabs to which one of the conductive wires from the distal lead is attached, at least one of the conductive wires from at least one of the plurality of proximal leads is also attached. Each proximal lead has a proximal end and a distal end and includes a plurality of conductive contacts disposed along the proximal end with the conductive wires coupled to the conductive contacts and extending to the distal end of the proximal lead. Each distal lead has a proximal end and a distal end and includes a plurality of electrodes disposed along the distal end with the conductive wires coupled to the electrodes and extending to the proximal end of the distal lead. The method further includes partially encasing the connected pre junction element in a first non-conductive material; removing the runner(s) to electrically isolate the tabs from each other and to form a connected junction; and encasing exposed portions of the connected junction in a second non-conductive material.

A further embodiment is a lead arrangement including a plurality of proximal leads, at least one distal lead, and a junction disposed between the plurality of proximal leads and the at least one distal lead. Each proximal lead has a proximal end and a distal end and includes conductive contacts disposed along the proximal end and conductive wires coupled to the conductive contacts and extending to the distal end of the proximal lead. Each distal lead has a proximal end and a distal end and includes electrodes disposed along the distal end and conductive wires coupled to the electrodes and extending to the proximal end of the distal lead. The junction includes a series of contact elements disposed sequentially between the plurality of proximal leads and the at least one distal lead and a non-conductive material encapsulating the contact elements. Each of the contact elements defines a central lumen. At least some of the conductive wires of the at least one distal lead and the conductive wires of at least one of the plurality of proximal leads are electrically coupled by attachment to the plurality of contact elements of the junction. The conductive wires of at least one of the proximal leads pass through the central lumen of each of the contact elements and into the at least one distal lead to form some of the conductive wires of the at least one distal lead.

Yet another embodiment is a method of making a coupled lead arrangement. The method includes providing a series of contact elements disposed sequentially between a plurality of proximal leads and at least one distal lead. Each of the contact elements defines a central lumen. Each proximal lead has a proximal end and a distal end and includes conductive contacts disposed along the proximal end and conductive wires coupled to the conductive contacts and extending to the distal end of the proximal lead. Each distal lead has a proximal end and a distal end and includes electrodes disposed along the distal end and conductive wires coupled to the electrodes and extending to the proximal end of the distal lead. The method further includes attaching exposed ends of a plurality of the conductive wires from at least one of a plurality of proximal leads and from at least one distal lead to the contact elements to form a connected junction. For each of the contact elements to which one of the conductive wires from the at least one distal lead is attached, at least one of the conductive wires from the at least one of the plurality of proximal leads is also attached. The method also includes passing a plurality of the conductive wires from at least one of the plurality of proximal leads through the central lumens of the contact elements and into the at least one distal lead to form some of the conductive wires of the at least one distal lead; and encasing the connected junction in a non-conductive material

BRIEF DESCRIPTION OF THE DRAWINGS

Non-limiting and non-exhaustive embodiments of the present disclosure are described with reference to the following drawings. In the drawings, like reference numerals refer to like parts throughout the various figures unless otherwise specified.

For a better understanding of the present disclosure, reference will be made to the following detailed description, which is to be read in association with the accompanying drawings, wherein.

Corresponding reference characters indicate corresponding components throughout the several views of the drawings.

DETAILED DESCRIPTION

The present invention is directed to the area of implantable electrical stimulation systems and leads and associated methods of making and using such systems and leads. More particularly, the present invention is directed to leads with connection junctions and methods of making and using such leads.

A lead can include at least one electrical conductive wire connecting one or more electrodes disposed on a distal end of the conductive wire, with one or more terminals disposed at one or more proximal ends of the conductive wire. Leads include, for example, percutaneous leads, paddle leads, and cuff leads. Examples of electrical stimulation systems with leads are present in, for example, U.S. Pat. Nos. 6,181,969; 6,516,227; 6,609,029; 6,609,032; and 6,741,892; 7,244,150; 7,672,734; 7,761,165; 7,949,395; 7,974,706; 8,175,710; 8,364,278; and U.S. Patent Application Publication No. 2007/0150036, all of which are incorporated herein by reference.

Figure 1:
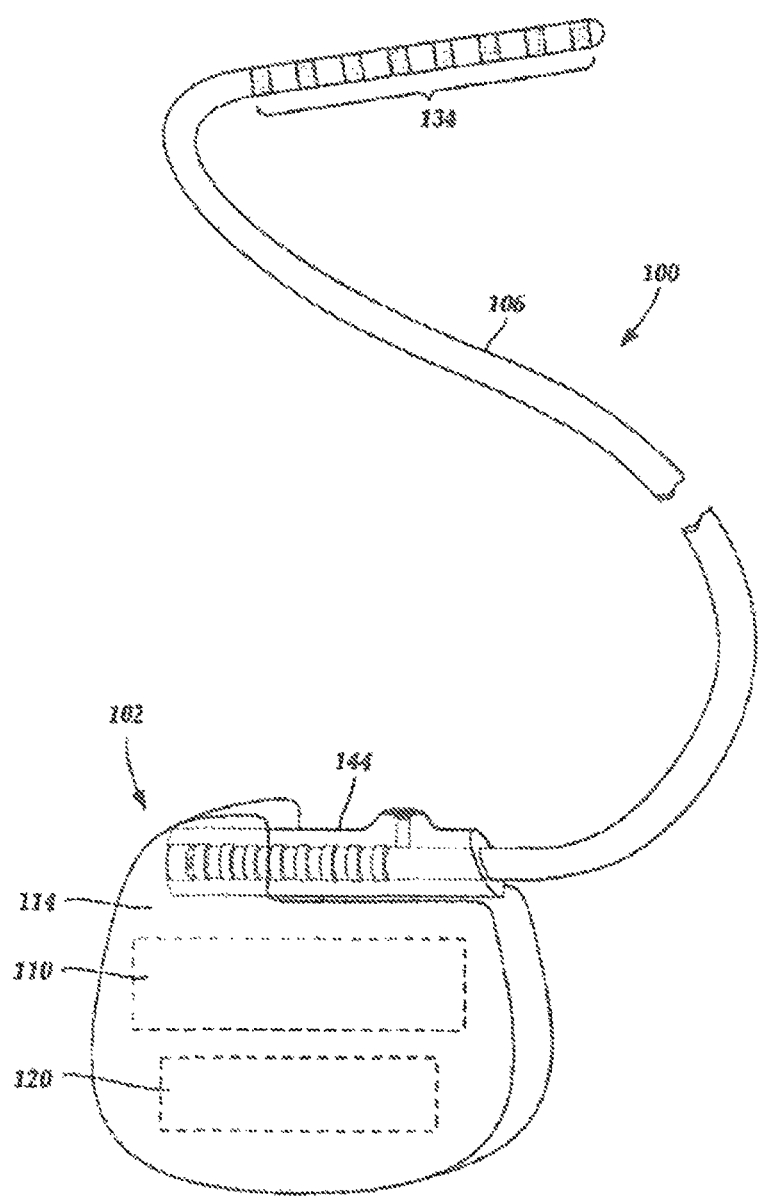
FIG. 1 is a schematic perspective view of one embodiment of an electrical stimulation system, according to the invention.

FIG. 1 illustrates schematically one embodiment of an electrical stimulation system 100. The electrical stimulation system includes a control module (e.g., a stimulator or pulse generator) 102 and at least one lead 106 coupled to the control module 102. Each lead 106 typically includes an array of electrodes 134. The control module 102 typically includes an electronic subassembly 110 and an optional power source 120 disposed in a sealed housing 114. The control module 102 typically includes one or more connectors 144 (FIG. 2A, see also 250 of FIG. 2B) into which the proximal end of the one or more leads 106 can be plugged to make an electrical connection via conductive contacts on the control module 102 and terminals 210 in (FIG. 2A) on each of the one or more leads 106. In at least some embodiments, a lead is isodiametric along a longitudinal length of the lead 106. In addition, one or more lead extensions 224 (see FIG. 2B) can be disposed between the one or more leads 106 and the control module 102 to extend the distance between the one or more leads 106 and the control module 102 of the embodiment shown in FIG. 1.

The electrical stimulation system or components of the electrical stimulation system, including one or more of the leads 106 and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. The number of electrodes 134 in the array of electrodes 134 may vary. For example, there can be two, four, six, eight, ten, twelve, fourteen, sixteen, or more electrodes 134. As will be recognized, other numbers of electrodes 134 may also be used.

The electrodes of one or more leads 106 are typically disposed in, or separated by, a non-conductive, biocompatible material such as, for example, silicone, polyurethane, polyetheretherketone ("PEEK"), epoxy, and the like or combinations thereof. The leads 106 may be formed in the desired shape by any process including, for example, molding (including injection molding), casting, and the like. The non-conductive material typically extends from the distal end of the one or more leads 106 to the proximal end of each of the one or more leads 106.

Terminals (e.g., 210 in FIGS. 2A and 236 of FIG. 2B) are typically disposed at the proximal end of the one or more leads 106 of the electrical stimulation system 100 for connection to corresponding conductive contacts (e.g., 214 in FIGS. 2A and 240 of FIG. 2B) in connectors (e.g., 144 in FIGS. 1-2A and 222 and 250 of FIG. 2B) disposed on, for example, the control module 102 (or to conductive contacts on a lead extension, an operating room cable, or an adaptor). Conductive wires (not shown) extend from the terminals (e.g., 210 in FIGS. 2A and 236 of FIG. 2B) to the electrodes 134. Typically, one or more electrodes 134 are electrically coupled to a terminal (e.g., 210 in FIGS. 2A and 236 of FIG. 2B). In at least some embodiments, each terminal (e.g., 210 in FIGS. 2A and 236 of FIG. 213) is only connected to one electrode 134. The conductive wires may be embedded in the non-conductive material of the lead 106 or can be disposed in one or more lumens (not shown) extending along the lead 106. In some embodiments, there is an individual lumen for each conductive wire. In other embodiments, two or more conductive wires may extend through a lumen. There may also be one or more lumens (not shown) that open at, or near, the proximal end of the lead 106, for example, for inserting a stylet rod to facilitate placement of the lead 106 within a body of a patient. Additionally, there may also be one or more lumens (not shown) that open at, or near, the distal end of the lead 106, for example, for infusion of drugs or medication into the site of implantation of the one or more leads 106. In at least one embodiment, the one or more lumens may be flushed continually, or on a regular basis, with saline, epidural fluid, or the like. In at least some embodiments, the one or more lumens can be permanently or removably sealable at the distal end.

Figure 2A:
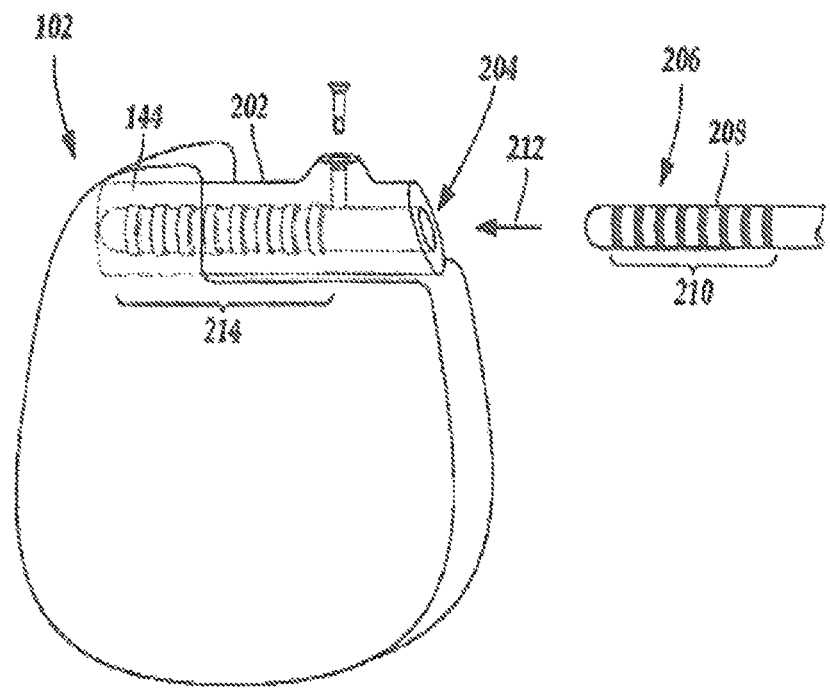
FIG. 2A is a schematic perspective view of one embodiment of a proximal portion of a lead and a control module of an electrical stimulation system, according to the invention.

In at least some embodiments, leads are coupled to connectors disposed on control modules. In FIG. 2A, a lead 208 is shown configured and arranged for insertion into the connector 144 of a control module 102. The connector 144 includes a connector housing 202. The connector housing 202 defines at least one port 204 into which a proximal end 206 of a lead 208 with terminals 210 can be inserted, as shown by directional arrow 212. The connector housing 202 also includes a plurality of conductive contacts 214 for each port 204. When the lead 208 is inserted into the port 204, the conductive contacts 214 can be aligned with the terminals 210 on the lead 208 to electrically couple the control module 102 to the electrodes (134 of FIG. 1) disposed at a distal end of the lead 208. Examples of connectors in control modules are found in, for example, U.S. Pat. Nos. 7,244,150 and 8,224,450, which are incorporated by reference.

Figure 2B:
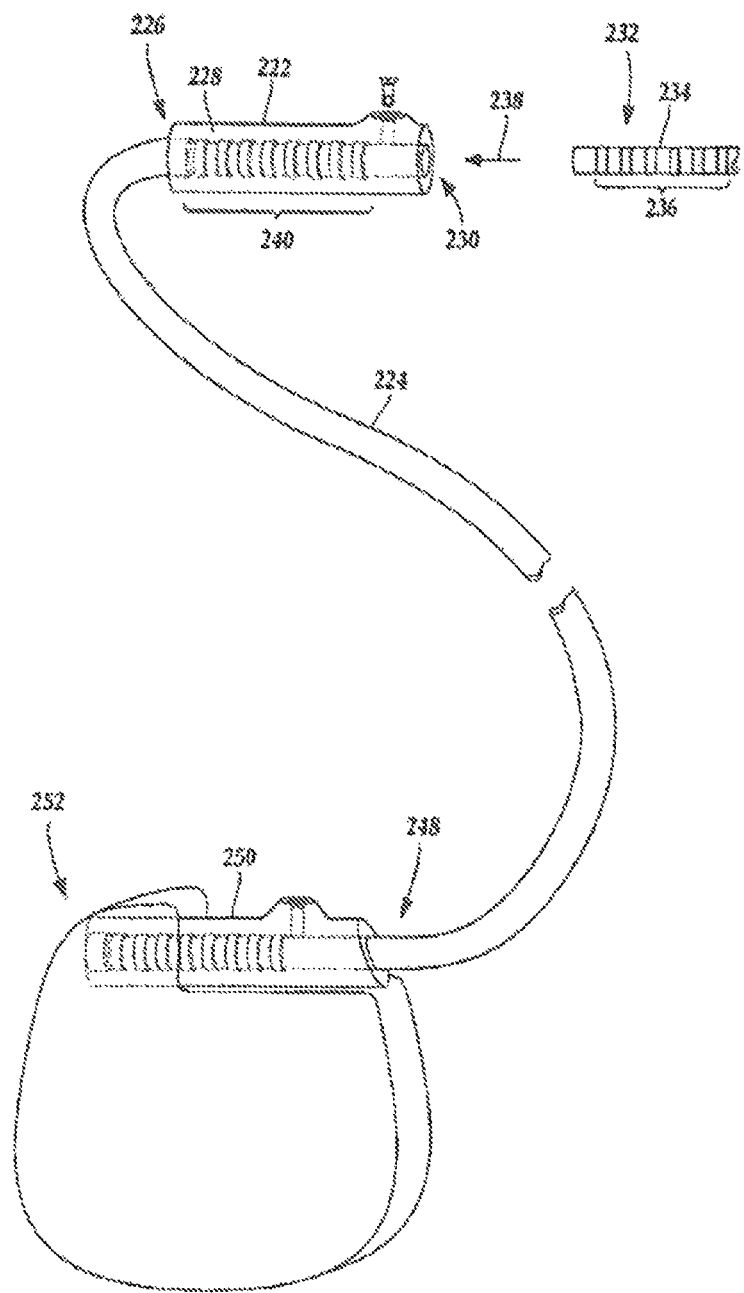
FIG. 2B is a schematic perspective view of one embodiment of a proximal portion of a lead and a lead extension of an electrical stimulation system, according to the invention.

In FIG. 2B, a connector 222 is disposed on a lead extension 224. The connector 222 is shown disposed at a distal end 226 of the lead extension 224. The connector 222 includes a connector housing 228. The connector housing 228 defines at least one port 230 into which a proximal end 232 of a lead 234 with terminals 236 can be inserted, as shown by directional arrow 238. The connector housing 228 also includes a plurality of conductive contacts 240. When the lead 234 is inserted into the port 230, the conductive contacts 240 disposed in the connector housing 228 can be aligned with the terminals 236 on the lead 234 to electrically couple the lead extension 224 to the electrodes (134 of FIG. 1) disposed at a distal end (not shown) of the lead 234.

In at least some embodiments, the proximal end of a lead extension is similarly configured and arranged as a proximal end of a lead. The lead extension 224 may include a plurality of conductive wires (not shown) that electrically couple the conductive contacts 240 to terminals on a proximal end 248 of the lead extension 224 that is opposite to the distal end 226. In at least some embodiments, the proximal end 248 of the lead extension 224 may be configured and arranged for insertion into a connector disposed in another lead extension. In other embodiments, the proximal end 248 of the lead extension 224 may be configured and arranged for insertion into a connector disposed in a control module. As an example, in FIG. 2B, the proximal end 248 of the lead extension 224 is inserted into a connector 250 disposed in a control module 252.

Sometimes a patient may experience pain emanating from an area greater in length than the length of an array of electrodes (e.g., electrodes 134 of FIGS. 1 and 2) disposed on the distal end of a lead. For example, a patient may experience pain in an area spanning multiple vertebral bodies. One way to increase stimulation coverage is to provide a lead with a greater length and either increase the amount of space between adjacent electrodes, or increase the size of one or more of the electrodes. However, when the amount of space between adjacent electrodes is increased or the size of one or more of the electrodes in increased, linear electrode density may decrease to a sub-therapeutic level.

Another way to increase stimulation coverage is to provide a lead with a greater length and increase the number of electrodes on the lead. However, a lead with additional electrodes may also need an increased number of conductive wires to electrically couple the electrodes to a control module. When an increased number of conductive wires are utilized in a lead, the lead may become incompatible with existing control modules. For example, the number of terminals disposed on the lead may exceed the number of corresponding connective contacts disposed in the control module. One option for facilitating compatibility between a lead and a control module is to couple a proximal end of the lead to a lead adaptor that attaches to two or more lead extensions, each lead extension coupled through the lead adapter to only some of the electrodes of the lead. The proximal end of each lead extension is received into a different connector port of the control module.

In at least some embodiments, stimulation coverage is increased by increasing the number of electrodes disposed at the distal end of a lead, preferably without increasing the lateral circumference of a distal end of the lead. In at least some embodiments, a lead includes a junction coupling the distal end of the lead with two or more proximal ends. Conductive wires disposed in the distal end of the lead are split at the junction into two or more groupings of conductive wires. Each grouping of conductive wires is disposed in a different proximal end. Each proximal end is configured and arranged to electrically couple at least one of the conductive wires disposed in the proximal end to at least one conductive contact disposed in a connector of a control module.

Figure 3:
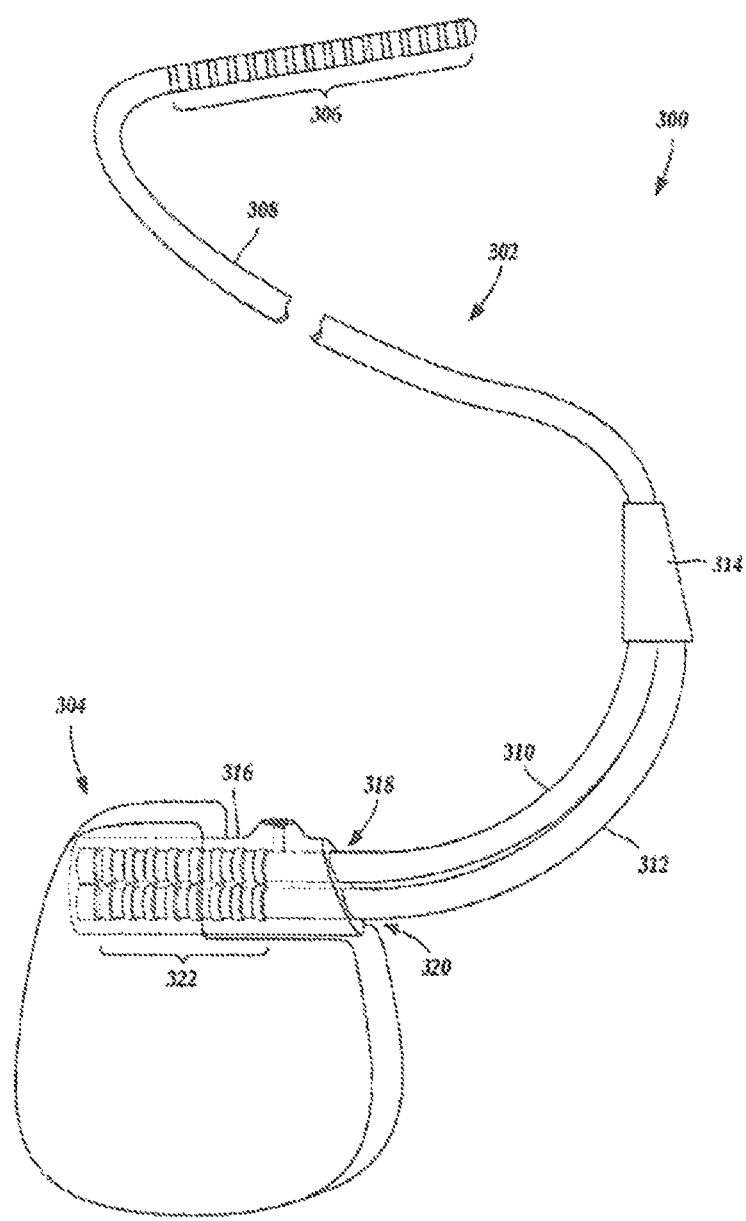
FIG. 3 is a schematic perspective view of one embodiment of an electrical stimulation system with a lead that includes multiple proximal ends coupled to a control module, according to the invention.

In at least some embodiments, each proximal end is coupled to a different connector port of a single control module. FIG. 3 is a schematic view of one embodiment of an electrical stimulation system 300 that includes a lead 302 and a control module 304. The lead 302 includes a plurality of electrodes 306 disposed at a distal end 308 and a plurality of terminals (not shown) disposed on each of a plurality of proximal ends 310 and 312. A junction 314 couples the distal end 308 to the plurality of proximal ends 310 and 312. The insulative portion of the junction 314 can be made using any non-conductive material suitable for implantation including, for example, silicone, polyurethane, PEEK, epoxy, and the like or combinations thereof. In at least some embodiments, the junction 314 may also provide mechanical sealing of any conductive wires disposed within the junction 314 to ameliorate current leakage.

In FIG. 3 and in other figures, two proximal ends are shown as a representation of a plurality of proximal ends for clarity of illustration. The plurality of proximal ends includes at least a first proximal end and a second proximal end and may include one or more additional proximal ends. In FIG. 3, the plurality of proximal ends includes a first proximal end 310 and a second proximal end 312. In some embodiments, the lead can include more than two proximal ends. For example, there can be one, two, three, four, five, six, seven, eight, nine, ten, twelve, fourteen, sixteen, or more proximal ends. As will be recognized, other numbers of proximal ends may also be used.

The control module 304 includes a connector 316 that defines a plurality of ports 318 and 320 configured and arranged to receive the first proximal end 310 and the second proximal end 312. In at least some embodiments, the number of ports is equal to the number of proximal ends of the lead 302. A plurality of conductive contacts 322 are disposed in each of the ports 318 and 320 and are configured and arranged to electrically couple the control module 304 to the electrodes 306. In at least some embodiments, conductive wires are routed to either the first proximal end 310 or the second proximal end 312 at the junction 314. In at least some embodiments, the length of the distal end 308 is substantially greater than the length of the first proximal end 310 and the second proximal end 312. In at least some embodiments, the first proximal end 310 and the second proximal end 312 are also configured and arranged to couple with other devices, such as lead extensions, adaptors, operating room cables, and the like or combinations thereof. In FIG. 3, the ports 318 and 320 are shown arranged vertically on the control module 304. In alternate embodiments, the ports 318 and 320 are arranged in other orientations, such as side-by-side, or on different sides of the control module 304.

In at least some embodiments, the number of conductive wires disposed in each of the proximal end is equal. In at some of these embodiments, the number of terminals disposed along each proximal end is equal. In other embodiments, one or more of the proximal ends have different numbers of conductive wires or different numbers of terminals (or both different numbers of conductive wires and terminals) with respect to on or more other proximal ends. In one embodiment, the lead 302 includes sixteen electrodes 306 electrically coupled with eight terminals (see e.g., 714 in FIG. 7) disposed along the first proximal end 310 and eight terminals (see e.g., 716 in FIG. 7) disposed along the second proximal end 312. Accordingly, in one embodiment, sixteen conductive wires are disposed in the distal end 308 of the lead 302 and are split into two groupings of eight conductive wires each at the junction 314. Eight conductive wires are disposed in the first proximal end 310 and eight conductive wires are disposed in the proximal end 312. In this embodiment, the corresponding connector 316 of the control module includes sixteen conductive contacts 322 configured and arranged with eight conductive contacts 322 disposed in each of the two ports 318 and 320 to electrically couple with the eight terminals disposed on each of the first proximal end 310 and the second proximal end 312 when the first proximal end 310 and the second proximal end 312 are inserted into the ports 318, 320, respectively.

Figure 4:
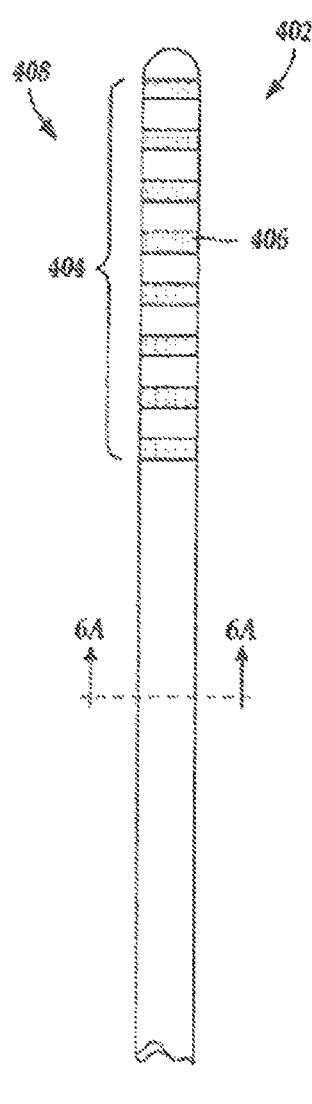
FIG. 4 is a schematic side view of one embodiment of a portion of a distal end of a conventional lead of an electrical stimulation system, according to the invention.

FIG. 4 is a schematic side view of one embodiment of a portion of a distal end of an exemplary conventional lead 402. The exemplary conventional lead 402 includes a plurality of electrodes 404, such as electrode 406, disposed on a distal end 408 of the exemplary conventional lead 402. Additional features of the exemplary conventional lead 402 are described below, with respect to FIG. 6A, for comparison with at least some embodiments.

Figure 5:
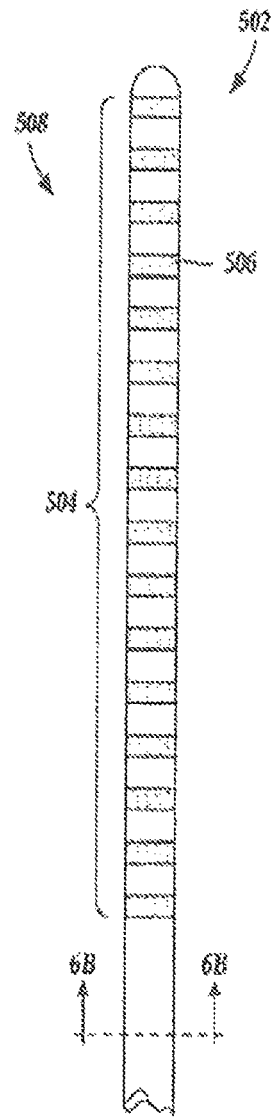
FIG. 5 is a schematic side view of another embodiment of a portion of a distal end of a lead of an electrical stimulation system, according to the invention.

FIG. 5 is a schematic side view of one embodiment of a portion of a distal end of a lead 502 with a lateral circumference that is equal to the lateral circumference of the exemplary conventional lead 402, but that includes twice the number of electrodes from the exemplary conventional lead 402. The lead 502 includes a plurality of electrodes 504, such as electrode 506, disposed along a distal end 508 of the lead 502. The plurality of electrodes 504 is greater than the plurality of electrodes 404 in FIG. 4 without a corresponding increase in the lateral circumference of the lead 502. In at least some embodiments, the portion of the lead 502 distal to the junction (314 in FIG. 3) is isodiametric. In one particular embodiment, the lead 502 has a lateral nominal diameter of 0.053 inches (0.135 cm). In at least some embodiments, the lead includes a paddle at its distal end with the electrodes disposed on the paddle. Such a lead may be isodiametric between the junction and the paddle.

Figure 6A:
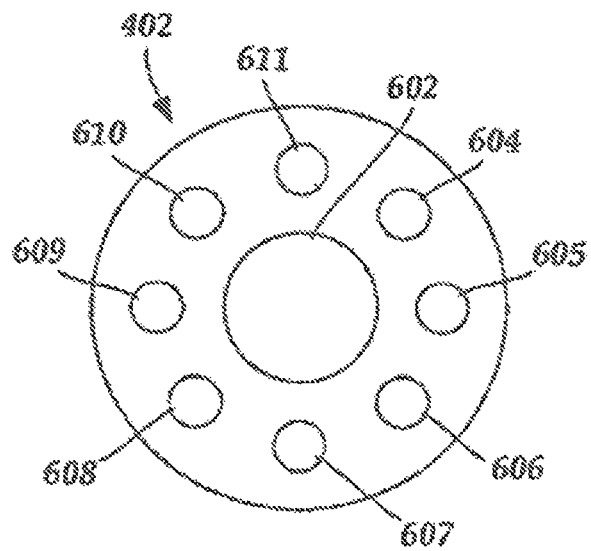
FIG. 6A is a schematic transverse cross-sectional view of one embodiment of the distal end of the lead shown in FIG. 4, according to the invention.

Conductive wires are used to electrically couple electrodes on a distal end of a lead to terminals on a proximal end of a lead. As discussed above, with reference to FIG. 1, conductive wires may be embedded in the non-conductive material of the lead or can be disposed in one or more lumens extending along the lead. In at least some embodiments, each individual conductive wire is disposed in an individual lumen. FIG. 6A is a schematic transverse cross-sectional view of the distal end of the exemplary conventional lead 402 shown in FIG. 4. In FIG. 6A, the exemplary conventional lead 402 includes a center lumen 602 and a plurality of outer lumens 604-611. Each outer lumen 604-611 is configured and arranged for an individual conductive wire to extend along the length of each individual outer lumen 604-611. In FIG. 6A, eight circular-shaped outer lumens 604-611 are shown. Thus, in the exemplary conventional lead 402 shown in FIG. 4, eight connector wires can be disposed in the outer lumens 604-611 and electrically coupled to eight electrodes.

Figure 6B:
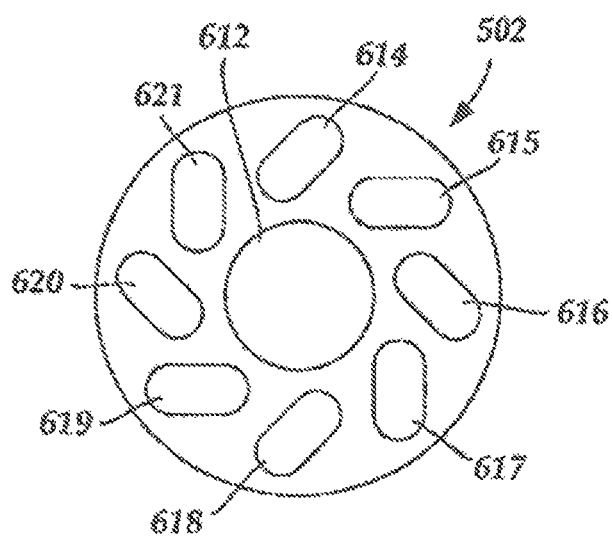
FIG. 6B is a schematic transverse cross-sectional view of one embodiment of the distal end of the lead shown in FIG. 5, according to the invention.

FIG. 6B is a schematic transverse cross-sectional view of one embodiment of the distal end of the lead 502. In FIG. 6B, the lead 502 includes a center lumen 612 and a plurality of outer lumens 614-621. Each outer lumen 614-621 is configured and arranged for multiple conductive wires to extend along the length of each individual outer lumen 614-621. In FIG. 6B, eight oval-shaped outer lumens 614-621 are shown, with each outer lumen 614-621 configured and arranged for two conductive wires to extend within each outer lumen 614-621. Thus, in some embodiments, sixteen connector wires can be disposed in the outer lumens 614-621 and electrically coupled to sixteen electrodes.

In alternate embodiments, outer lumens can be configured and arranged to accommodate one conductive wire or more than two conductive wires. Accordingly, the number of multiple conductive wires that can be disposed in an outer lumen may vary. For example, there can be one, two, three, four, five, six, seven, eight, nine, ten, twelve, fourteen, sixteen, or more conductive wires disposed in an outer lumen. As will be recognized, other numbers of conductive wires may also be disposed in an outer lumen.

Figure 7:
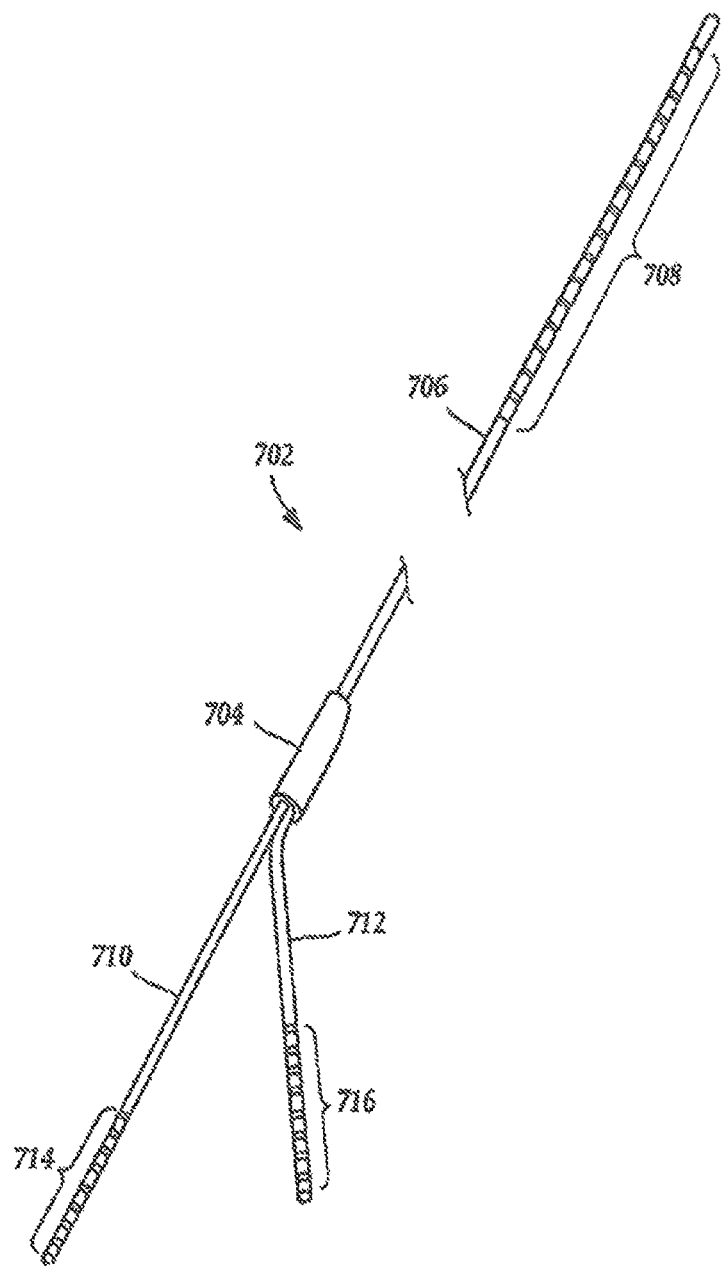
FIG. 7 is a schematic perspective view of one embodiment of a lead with a junction coupling a distal end of the lead to a plurality of proximal ends, according to the invention.

FIG. 7 is a schematic perspective view of one embodiment of a lead 702 with a junction 704 coupling a distal end 706 with electrodes 708 disposed along the distal end 706 to a first proximal end 710 and a second proximal end 712. The first proximal end 710 includes terminals 714 disposed along the first proximal end 710 and the second proximal end 712 includes terminals 716 disposed along the second proximal end 712. In at least some embodiments, the first proximal end 710 and the second proximal end 712 are each configured and arranged for insertion into one of a plurality of ports defined in a connector that is electrically coupled to a control module. In at least some embodiments, the number of terminals 714 disposed on the first proximal end 710 is equal to the number of terminals 716 disposed on the second proximal end 712. In at least some embodiments, the collective number of terminals 714 and 716 disposed on both the first proximal end 710 and the second proximal end 712, respectively, is equal to the number of electrodes 708 disposed on the distal end 706 of the lead 702.

Figure 8A:
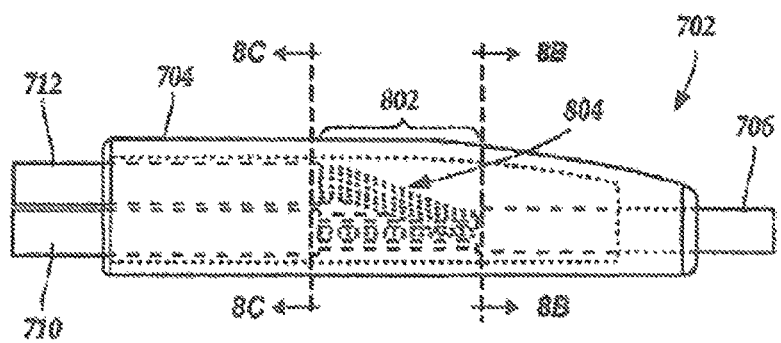
FIG. 8A is a close-up schematic side view of one embodiment of the junction of the lead shown in FIG. 7, according to the invention.

FIG. 8A is a schematic side view of one embodiment of the junction 704 disposed on the lead 702. The junction 704 couples the distal end 706 with the first proximal end 710 and the second proximal end 712. In at least some embodiments, the lateral diameter of the junction 704 is greater than the lateral diameter of the distal end 706 of the lead 702. A longitudinal schematic cross-sectional view of a conductive-wire branching region 802 is shown disposed within the junction 704. In FIG. 8A, a plurality of conductive wires 804 are shown branching from the distal end 706 to each of the first proximal end 710 and the second proximal end 712.

Figure 8B:
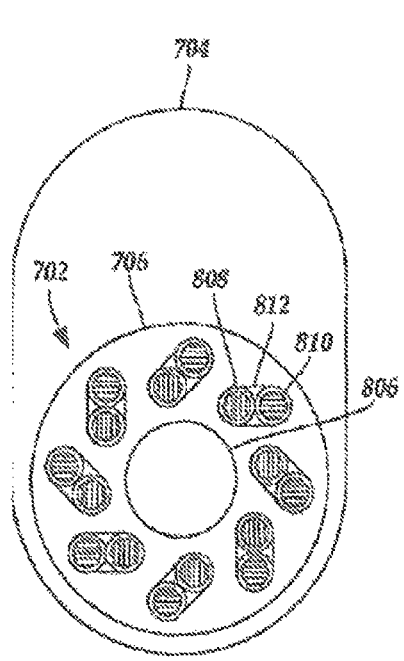
FIG. 8B is a schematic cross-sectional view along line 8B-8B of the junction shown in FIG. 8A, according to the invention.
Figure 8C:
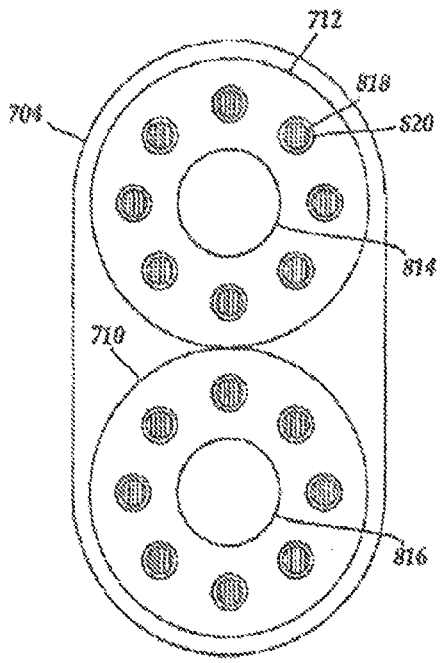
FIG. 8C is a schematic cross-sectional view along line 8B-8B of the junction shown in FIG. 8A, according to the invention.

In at least some embodiments, the number of conductive wires disposed in the distal end 806 is equal to the collective number of conductive wires disposed in both the first proximal end 808 and the second proximal end 810 and the number of conductive wires disposed in the first proximal end 808 is equal to the number of conductive wires disposed in the second proximal end 810. For example, as shown in FIGS. 8A-8C, sixteen conductive wires are shown disposed in the distal end 806 that split evenly into eight conductive wires disposed in both the first proximal end 808 and the second proximal end 810. In other embodiments, other numbers of conductive wires may be used, as well. For example, thirty-two conductive wires may be disposed in the distal end that split into a first proximal end and a second proximal end with sixteen conductive wires disposed in both the first proximal end and the second proximal end. In an alternate embodiment, thirty-two conductive wires disposed in the distal end may split into four proximal ends with eight conductive wires disposed in each of the proximal ends.

In at least some embodiments, the junction includes arrangement with conductive tabs; each tab having attached thereto a wire (or multiple wires) from the distal end and a wire (or multiple wires) from one of the proximal ends. These tabs are encased by a non-conductive material (e.g., plastic material) which, at least in some embodiments, is molded around the tabs and attached wires. The junction may be formed from a pre junction element with the tabs connected by a runner that is removed during manufacture. In some embodiments, the runner is removed after disposing plastic material around a portion of each tab to hold the tabs in place. The remainder of the plastic material may be formed after removing the runner. The wires from the distal end and proximal ends may be coupled to the tabs prior to removing the runner or after removing the runner. The wires from the distal end and proximal ends may be coupled to the tabs prior to, or after, disposing plastic material around the portion of tab.

Any suitable pre junction element can be used including, but not limited to, a rib cage element, a square rib cage element, a metal ladder, or any similar structures. These pre junction elements are formed from a conductive material, such as, for example, a hypo tube or any other suitable construct. In at least some embodiments, the pre junction element is partially encased in an insulating material during a first molding phase. The runner is removed after the first molding phase. Thereafter, the partially-encased tabs are molded again in an insulating material, in order to encase the portions of the junction that were not encased during the first molding phase, thereby insulating the tabs, and conductive wires attached to the tab, from other tabs and their associated conductive wires.

Figure 9A:
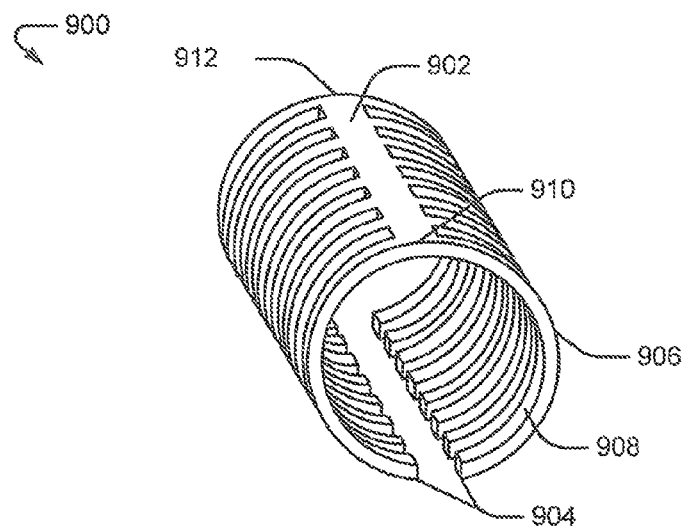
FIG. 9A is a schematic perspective view of one embodiment of a rib cage pre junction element, according to the invention.

FIG. 9A is a perspective view of one embodiment of a rib cage pre junction element 900. The rib cage pre junction element 900 may be formed, for example, from a hypo-tube and may be made of a metal, such as Nitinol™, titanium, stainless steel, or the like. In one embodiment, the rib cage pre junction element 900 is laser cut from the hypo-tube, while another embodiment employs a 3D printing technique to generate the pre junction element.

The rib cage pre junction element 900 has a proximal end 910 and a distal end 912 and a runner or spine 902 joining the proximal end 910 and the distal end 912. As shown, the rib cage pre junction element 900 includes a number of rib-like structures that form tabs 904 arranged in one or more rows. In one embodiment of the present disclosure, the rib cage pre junction element 900 has at least sixteen tabs 904 arranged in two rows. FIG. 9A shows only two rows of tabs 904, but those in the art will that there may be more than two rows of tabs 904. Each of the tabs 904 has an outside surface 906 and an inside surface 908. The runner 902 imparts stiffness and stability to the overall structure of rib cage pre junction element 900, holding individual tabs 904 in position relative to one another during the manufacturing process.

Figure 9B:
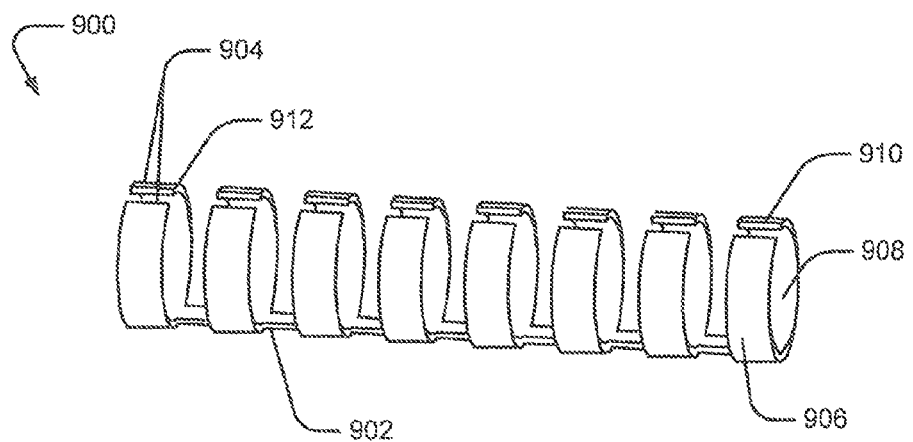
FIG. 9B is a schematic side view of the rib cage pre junction element of FIG. 9A.
Figure 9C:
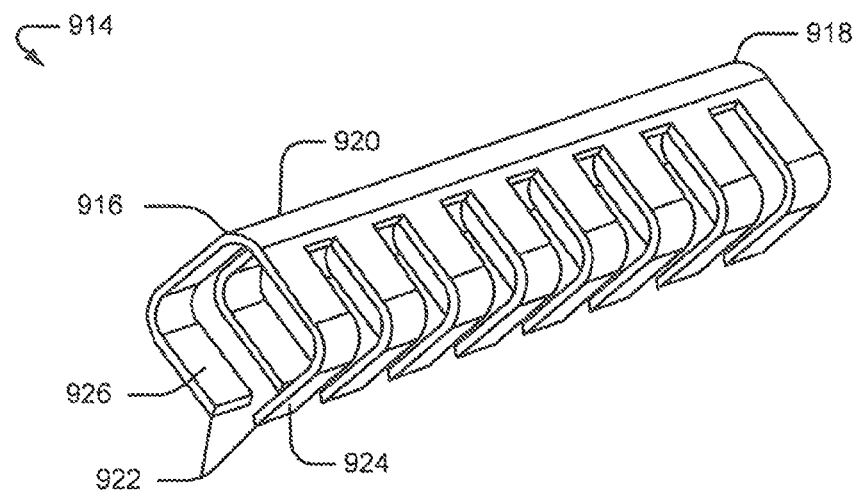
FIG. 9C is a schematic perspective view of one embodiment of a square rib cage pre-junction element, according to the invention.

FIG. 9B is a side view of the rib cage pre junction element 900. In the illustrated embodiment, the rib cage pre junction element 900 presents a generally circular cross-section. In other embodiments, the cross-section of the rib cage pre junction element 900 may be non-circular. For example, a rib cage pre junction element may have a square cross-section as shown in FIG. 9C. The square cross-section rib cage pre junction element 914 has a proximal end 916 and a distal end 918, with one or more tabs 922 interconnected by a runner 920. Each of the tabs 922 has an outside surface 924 and an inside surface 926. The square cross-section rib cage pre-junction element 914 may provide for easier welding, as the tabs 922 define flat surfaces.

Figure 10:
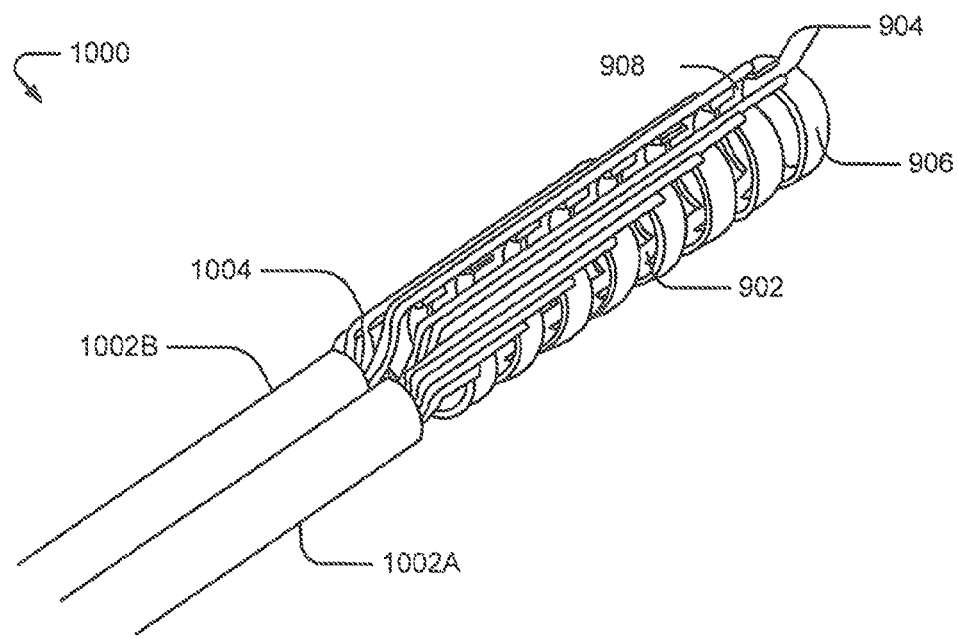
FIG. 10 is a schematic perspective view of the rib cage pre junction element of FIG. 9A with conductive wires from a two proximal leads attached, according to the invention.

FIG. 10 depicts a rib cage pre junction element 1000 connected to conductive wires 1004 of at least two proximal leads 1002A-1002B. As shown, the two proximal leads 1002A, 1002B each include multiple conductive wires 1004. In one embodiment, each of the proximal leads 1002 includes eight conductive wires 1004. Each conductive wire 1004 may be connected to a single tab 1004, with conductive wires 1004 extending along the rib cage pre junction element 1000 to its tab 1004. Each conductive wire includes insulation disposed around the conductive wire, except at the end where it is attached to its tab, to prevent shorting with other tabs. The conductive wires 1004 may be connected to the tabs 904 by, for example, welding, brazing, soldering, and so forth. Various examples of suitable welding processes include, but are not limited to, laser beam welding, electron beam welding, explosion welding, gas welding, arc welding, chemical welding, and the like. FIG. 10 shows conductive wires 1004 as connected or welded to the outside surfaces 1006 of the tabs 904. In another embodiment, the conductive wires 1004 may be connected or welded to the inside surfaces 1008 of the tabs 904.

Figure 11A:
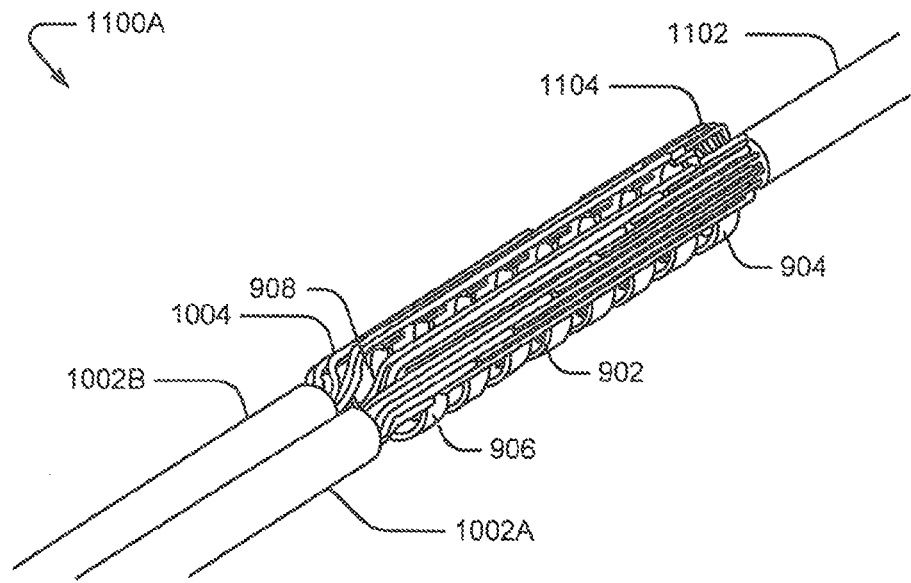
FIG. 11A is a schematic perspective view of the rib cage pre junction element of FIG. 9A with conductive wires from a two proximal leads and from one distal lead attached, according to the invention.

Similarly, as shown in FIG. 11A, multiple conductive wires 1104 of one or more distal leads 1102 can be joined to the tabs 904 by using any suitable attachment process. FIG. 11A shows a pictorial view of a pre junction element 1100A connected to conductive wires of the two proximal leads 1002 and one distal lead 1102. As shown, the connected pre junction element 1100 includes proximal conductive wires 1004 and distal conductive wires 1104, both connected to tabs 904. The conductive wires 1104 and 1004 are connected to the tabs 904 such that at least one conductive wire 1004 and one conductive wire 1104 are connected to each of the tabs 904. In this way, the distal lead 1102 will connect to the proximal leads 1002A-B. In one embodiment, the distal lead 1102 includes sixteen conductive wires 1104, each connected to outside surfaces 906 of tabs 904. Alternatively, the conductive wires 1104 may be connected or welded on the inside surfaces 908 of the tabs 904. The proximal leads 1002 are lateral and the distal lead 1102 is medial in this arrangement because the distal lead 1102 is connected second.

Therefore, this arrangement keeps the proximal leads 1002 out of the way while connecting the distal lead 1102.

Figure 11B:
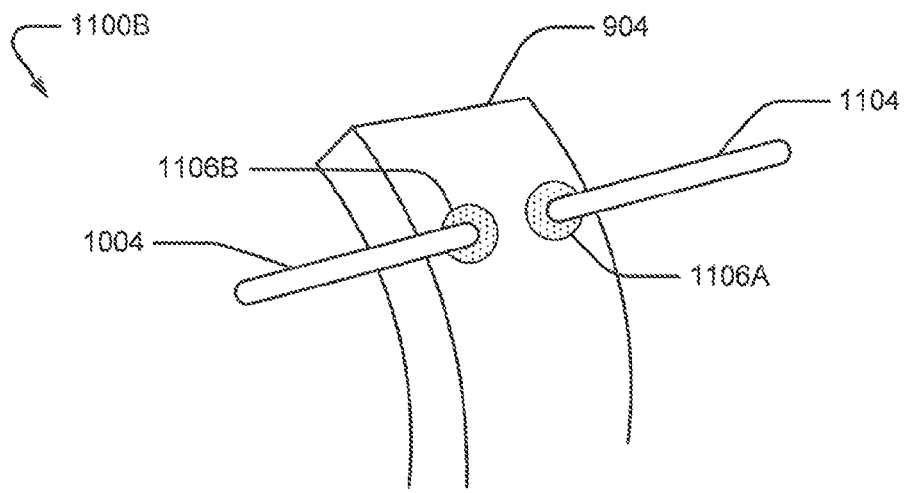
FIG. 11B is a side view of conductive wires from a proximal lead and a distal lead attached to a tab of a pre junction element, according to the invention.

FIG. 11B is a detailed perspective view of a proximal lead conductive wire 1004 and a distal lead conductive wire 1104 connected to at least one of the tabs 904. The distal conductive wires 1104 may be connected (or welded) to the rib cage pre junction element 900 after connecting the proximal conductive wires 1004 to avoid any interference between the two sets of conductive wires. The attachment process produces a distal contact 1106A, where one of the distal conductive wires 1104 connects to the at least one of the tabs 904, and a similar proximal contact 1106B where the proximal conductive wire 1004 connects to the same tab 904.

Figures 12A, 12B:
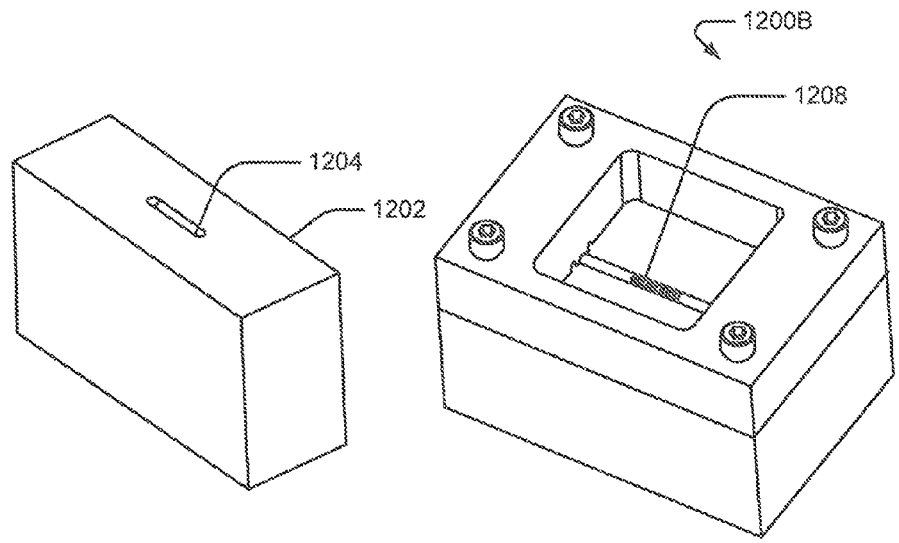
FIGS. 12A-12B are schematic perspective views of embodiments of welding block(s) used for connecting the conductive wires to tabs of the pre junction element, according to the invention.
Figure 12C:
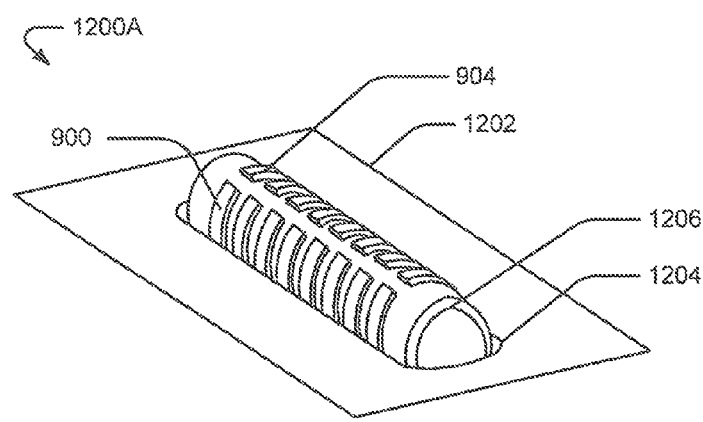
FIG. 12C is a schematic perspective view of a pre junction element disposed in a mold, according to the invention.

In at least some embodiments, the conductive wires 1004 and 1104 are connected to the tabs 904 by welding. A welding block 1202, as shown in FIG. 12A, having at least one welding support pin 1204, may be used for welding the conductive wires 1004 or 1104 onto the tabs 904. As shown, the welding block 1202 has a semi-circular cross-sectional welding support pin 1206, shown in FIG. 12B, that supports the rib cage pre junction element 900 during the welding process. The shape, size, and cross-section of the welding support pin 1206 may differ depending on the shape and size of the pre junction element 900. In some embodiments, a metal pin 1206 such as a copper pin, an iron pin, or the like may be inserted inside the rib cage pre-junction element 900 during welding to prevent collapse of the tabs 904. The metal pin 1206 may also serve as a current sink.

Welding of conductive wires 1004 and 1104 to the rib cage pre junction element 900 may include special fixturing. FIG. 12B depicts a welding block 1200B having a special fixturing. The rib-cage pre junction element 900 may slide onto a metal mandrel 1208 so that pressure of resistance welder will not crush the rib-cage pre junction element 900. The mandrel 1208 may also serve as a low resistance current path, dispersing the current to the main body of the welding block 1200B. The fixture on the welding block 1200B includes two metal blocks that are screwed together to tightly sandwich the metal mandrel. The upper part of the sandwich may have a large hole in it to expose the rib-cage pre junction element 900 for welding. The upper part may also have slots for lead body passage.

Figure 13:
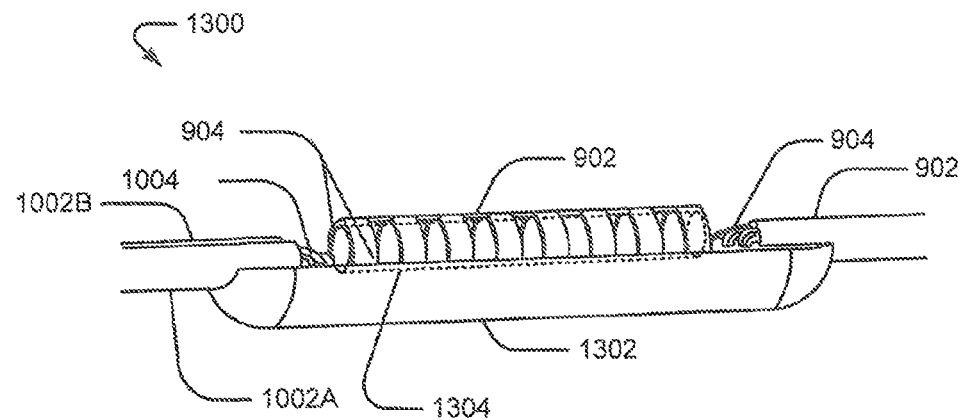
FIG. 13 is a schematic side view of one embodiment of a partially encased pre junction element, according to the invention.

After connecting the conductive wires 1004 and 1104 to the tabs 904, the connected pre-junction element 1100A may be partially encased in an insulating material 1302 using, for example, a first molding process. FIG. 13 illustrates a partially encased pre junction element 1300. In at least some embodiments, the connected pre junction element 1100 as shown in FIG. 11A may be partially encased by partially submerging it in a suitable insulating material to form a half-capsule 1302 (or other partial-capsule). This can be accomplished using, for example, a half mold (not shown) or an open-faced mold. In at least one embodiment, the material of the insulating capsule 1302 may be Hysol® epoxy or a similar medical grade epoxy. In at least some embodiments, the connected pre junction element 1100A can be placed in the mold in such a manner that the welds or connections face downwards in the open-faced mold. In one embodiment, a tube 1304 extending from the distal lead 1102 to one of the proximal leads 1002 is placed through the connected pre junction element 1100. The tube 1304 may allow for stylet passage or the like.

Figure 14:
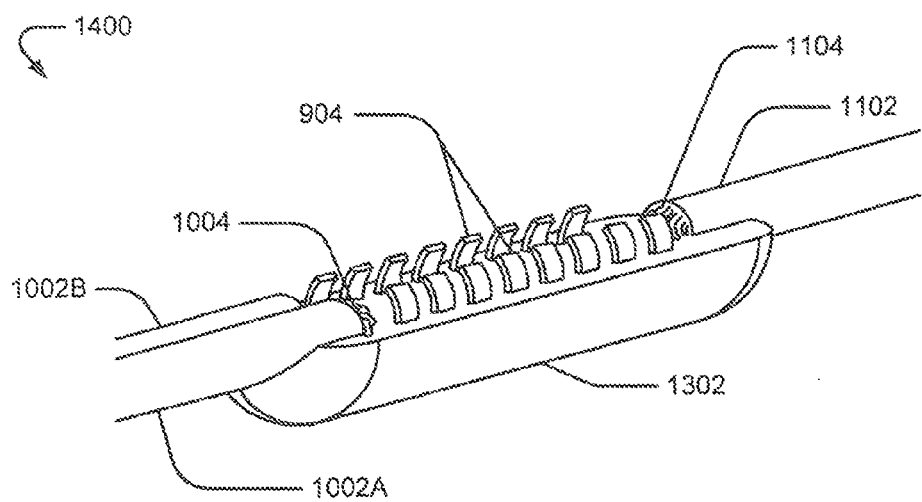
FIG. 14 is a schematic perspective view of the encased junction of FIG. 13 without the runner, according to the invention.

After the first encasing or molding stage, the runner 902 is removed from the encased pre junction element 1300. Removal can be accomplished by, for example, a mechanical or laser cutting operation or any other suitable method for removing the runner. FIG. 14 depicts a junction 1400 after the runner 902 has been removed. As discussed with reference to FIG. 10 and FIG. 11, removal of the runner 902 from the encased pre junction element 1300 of FIG. 13 electrically isolates the individual tabs, and their associated conductive wires, from other tabs and their associated conductive wires.

Figure 15:
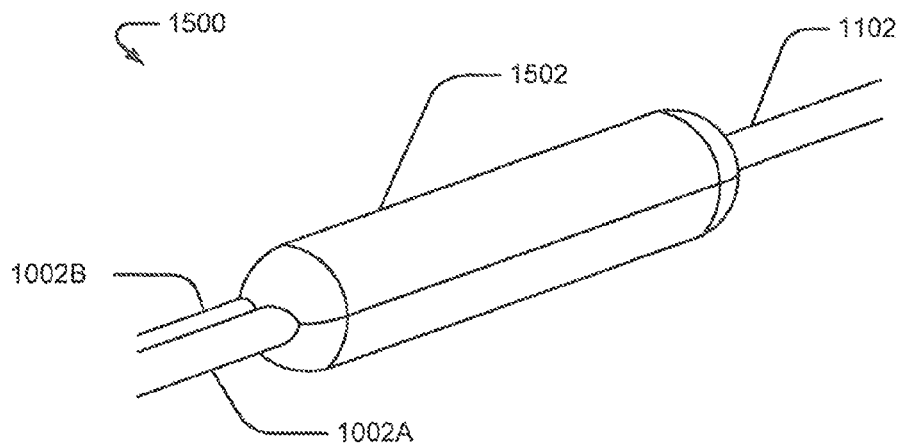
FIG. 15 is a schematic perspective view of a coupled lead arrangement formed using a rib cage pre junction element, according to the invention.

Thereafter, exposed parts of the tabs 904 are covered or encased in an insulating material 1502 (or an insulating capsule 1502) in, for example, a second molding stage. FIG. 15 depicts a coupled lead arrangement 1500 with the junction 1400 (FIG. 14) encased in the insulating capsule 1502. The coupled lead arrangement 1500 includes the tabs 904, from the pre junction element 900, connected to the conductive wires 1004 of the proximal leads 1002A, 1002B and the conductive wires 1104 of the distal lead 1102. In at least one embodiment, the junction 1400 is encased in Hysol® epoxy or another medical grade epoxy. In other embodiments, the junction 1400 may be encased in any other suitable material such as silicone, polyurethane, or the like.

Figure 16A:
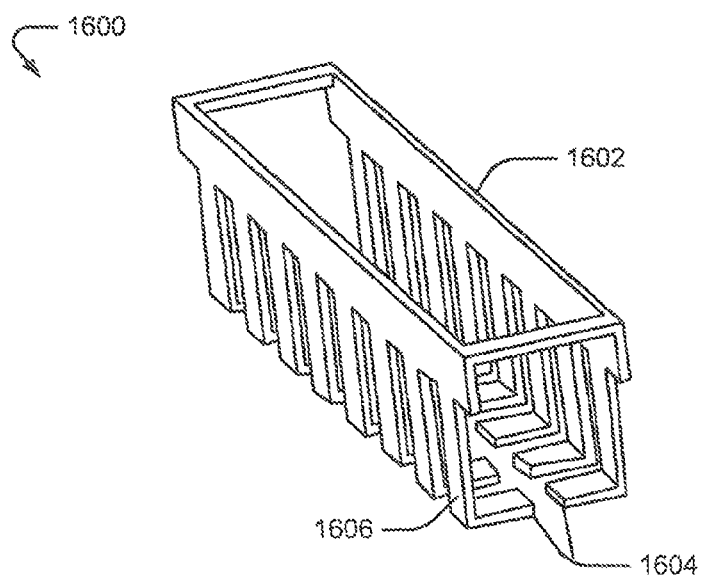
FIG. 16A is a schematic perspective view of one embodiment of a bent ladder pre-junction element, according the invention.
Figure 16B:
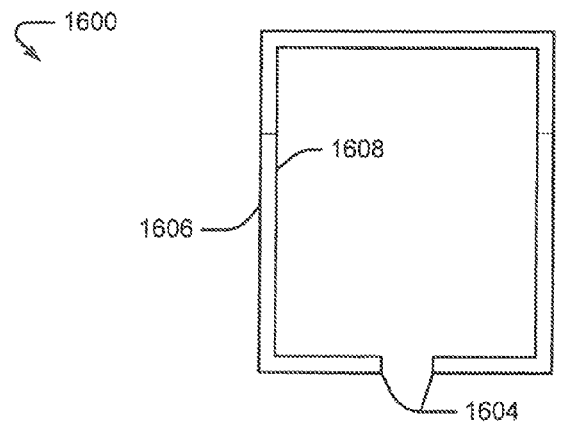
FIG. 16B is a schematic end view of the bent ladder pre junction element of FIG. 16A, according to the invention.

FIG. 16A is a schematic diagram of a bent ladder pre junction element 1600 that may be formed, for example, from a rectangular tube employing a process such as laser cutting or forming. This pre junction element includes a number of tabs 1604 arranged in one or more rows. In the embodiment illustrated in FIG. 16A, sixteen tabs 1604 are arranged in two opposing rows. The bent ladder pre junction element 1600 is made of a conductive material such as, for example, Nitinol™, titanium, stainless steel, and so forth. Each of the tabs 1604 has an outside surface 1606 and an inside surface 1608. The bent ladder pre junction element 1600 also includes a runner 1602 (or a spine) for holding the tabs 1604 in position during welding and molding. FIG. 16B illustrates an end view of the bent ladder pre junction element 1600. Conductive wires of various leads may be connected to the tabs 804.

Figure 17:
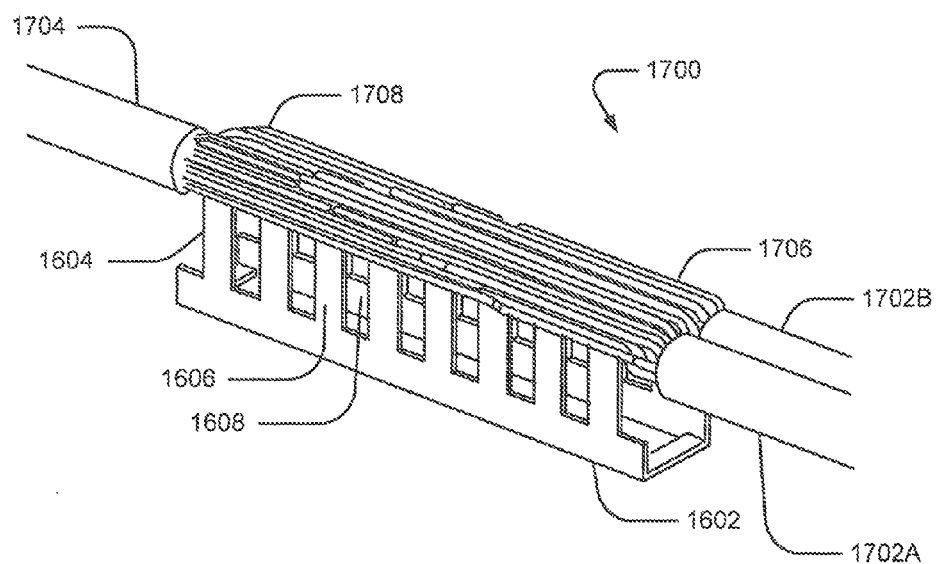
FIG. 17 is a schematic perspective view of a connected bent ladder pre junction element with attached conductive wires from two proximal leads and one distal lead, according to the invention.

FIG. 17 depicts a connected bent ladder pre junction element 1700 with a number of conductive wires 1706 of proximal leads 1702A-1702B (collectively, proximal leads 1702) and conductive wires 1708 of distal lead 1704 connected to the junction 1600 of FIG. 16A-16B. In one embodiment, each of the proximal leads 1702 includes at least eight conductive wires 1706 (hereinafter, proximal conductive wires 1706) and the distal lead 1704 includes sixteen conductive wires 1708. The conductive wires 1706 may be connected to the tabs 1604 of the junction 1600 such that only one conductive wire of the conductive wires 1706 is attached to each of the tabs 1604. Conductive wires 1708 of distal lead 1704 can be joined to the tabs 1604 using any suitable process such as, for example, welding, brazing, and the like. In this way, the distal contacts will be electrically connected with the proximal contacts. Since the distal conductive wires 1708 are welded or connected to the junction 1600 after connecting the proximal conductive wires 1706, the proximal conductive wires 1706 avoid interfering with distal conductive wires 1708. Further, FIG. 17 shows conductive wires 1706-1708 connected to the outer surfaces 1606 of the tabs 1604, but in other embodiments, the conductive wires 1706-1708 may be connected to the inner surfaces 1608 of the tabs 1604. A welding block having at least one welding support pin with a cross-section according to the shape and size of the junction 1600 may be used for welding the conductive wires onto the tabs 1604. In addition, a metal pin may be inserted into the junction 1600 to avoid collapsing of the junction 1600. Though only two proximal leads and one distal lead are shown in FIG. 17, it will be appreciated that more or less than two proximal leads can be connected to one or more distal leads.

Figure 18:
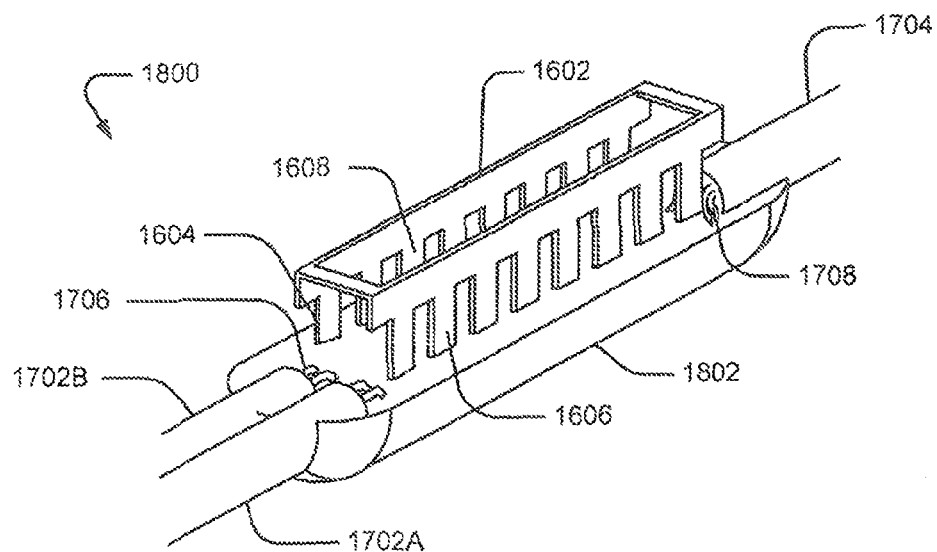
FIG. 18 is a schematic perspective view of one embodiment of a partially encased bent ladder pre junction element, according to the invention.

Thereafter, the pre junction element 1700 may be partially encased in an insulating material, forming an insulating capsule 1802. FIG. 18 illustrates a partially encased junction 1800. For example, the pre junction element 1700 may be placed in an open-faced mold, and insulating material such may fill the mold, partially encasing the connected pre junction element 1700. The material of the insulating capsule 1802 may be Hysol® epoxy or a similar medical grade epoxy, silicon, polyurethane, or any other suitable material. While encasing the pre-junction element 1700 1700, the welds and connections are facing downwards in the insulating capsule 1802.

Figure 19:
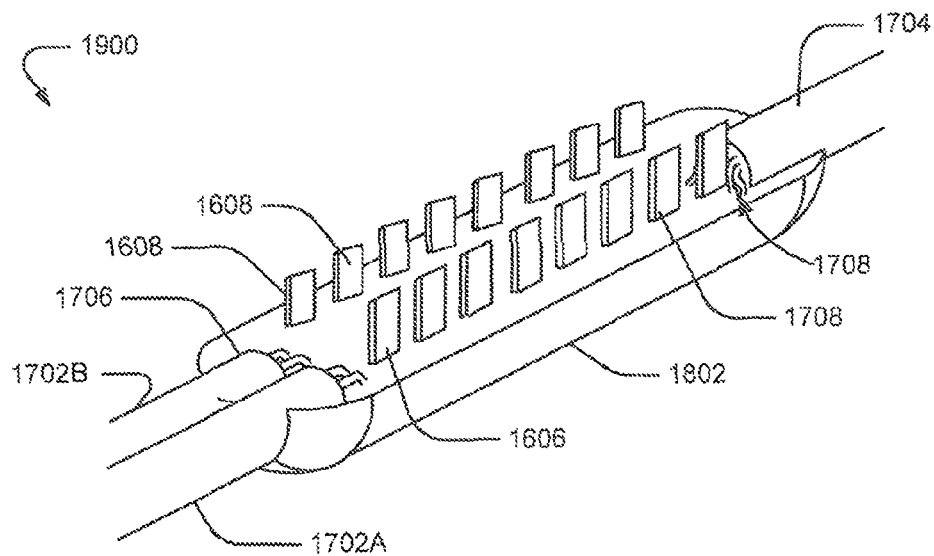
FIG. 19 is a schematic perspective view of the partially encased bent ladder pre junction element of FIG. 18 without a runner, according to the invention.

After the first encasing or molding stage of the pre junction element 1800, the runner 1602 is removed from the encased pre junction element 1800. FIG. 19 depicts a junction 1900 after the runner 1602 has been removed. As discussed with reference to FIG. 17, removal of the runner 1602 from the pre junction element 1800 electrically isolates conductive wire pair of the proximal leads 1702 and the distal lead 1704.

Figure 20:
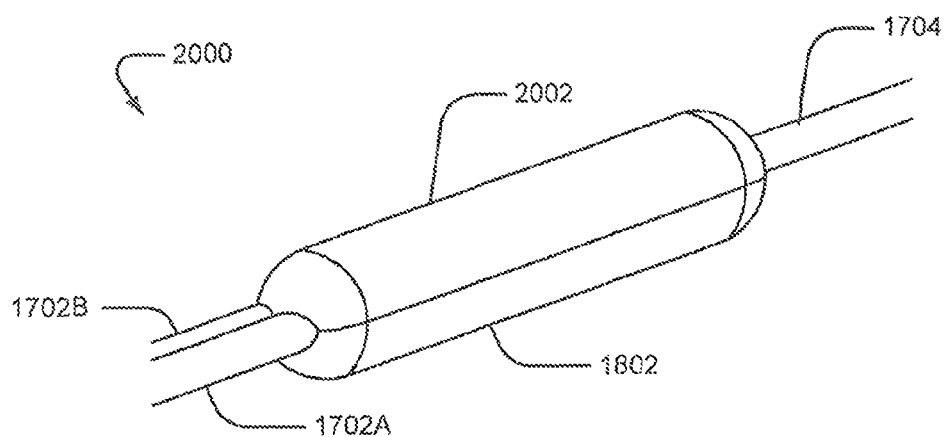
FIG. 20 is a schematic perspective view of a coupled lead arrangement formed using the bent ladder pre junction element of FIGS. 16A-16B, according to the invention.

Thereafter, exposed portion of each of the tabs 1604 may be covered or encased in another insulating capsule or a second mold 2002. FIG. 20 depicts a coupled lead arrangement 2000 formed by encasing the junction 1900 in the second mold 2002. In a second full molding stage, the exposed portion of each of the tabs 804 is encased in the insulating capsule 1902. Therefore, the coupled lead arrangement 2000 includes the junction 1900 connected to the conductive wires 1706 and the conductive wires 1708 that is encased at least twice. In an embodiment, the junction 1900 is encased in Hysol® epoxy or a similar medical grade epoxy, silicon, polyurethane, or any other suitable material. In another embodiment, the junction 1900 may be encased using any suitable insulating material.

Figure 21A:
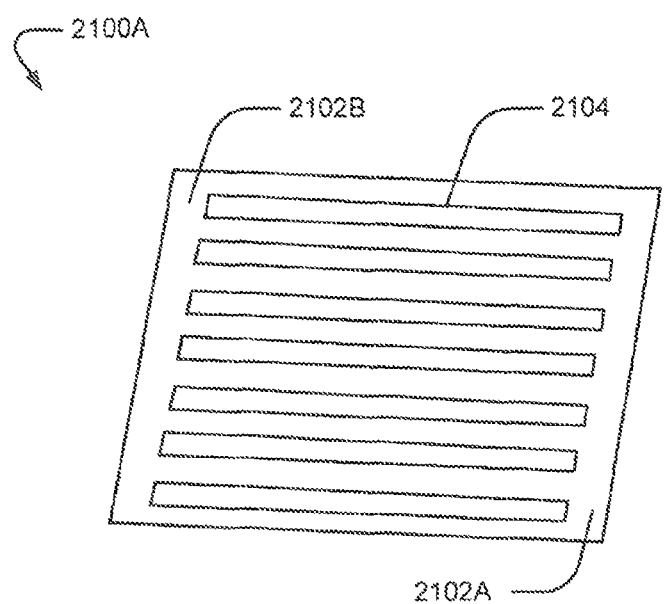
FIG. 21A is a schematic top view of one embodiment of a flat ladder pre junction element, according to the invention.
Figure 21B:
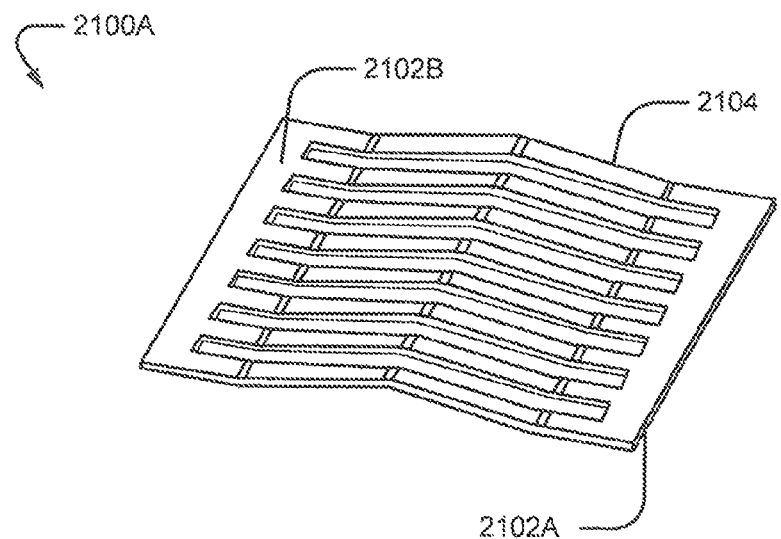
FIG. 21B is a schematic perspective view of another embodiment of a ladder pre-junction element bent to form an arch, according to the invention.

FIG. 21A is a schematic diagram of a metal ladder pre junction element 2100A, according to an embodiment of the present disclosure. The ladder pre junction element 2100A may be etched, stamped, or otherwise formed. Constructing a branched lead or a coupled lead arrangement using the ladder pre junction element 2100A would require two ladder pre junction elements 2100A and 2100B, as shown in FIG. 22. Each of the ladder pre junction elements 2100A-2100B includes eight tabs 2104A and 2104B respectively. In some embodiments, the ladder pre junction element 2100 may include less or more than eight tabs 2104. The middle portion of the ladder pre junction elements 2104A-2104B may be used as the tabs 2104. The ladder pre junction element 2100A has two runners i.e. a runner 2102A and a runner 2102B on two sides of the tabs 2104A. Similarly, the ladder pre junction element 2100B has at least two runners i.e. a runner 2102C and a runner 2102D extending along the two sides of the tabs 2104B. The ladder pre junction element 2100 may be bent to form an arch as shown in FIG. 21B.

Figure 22A:
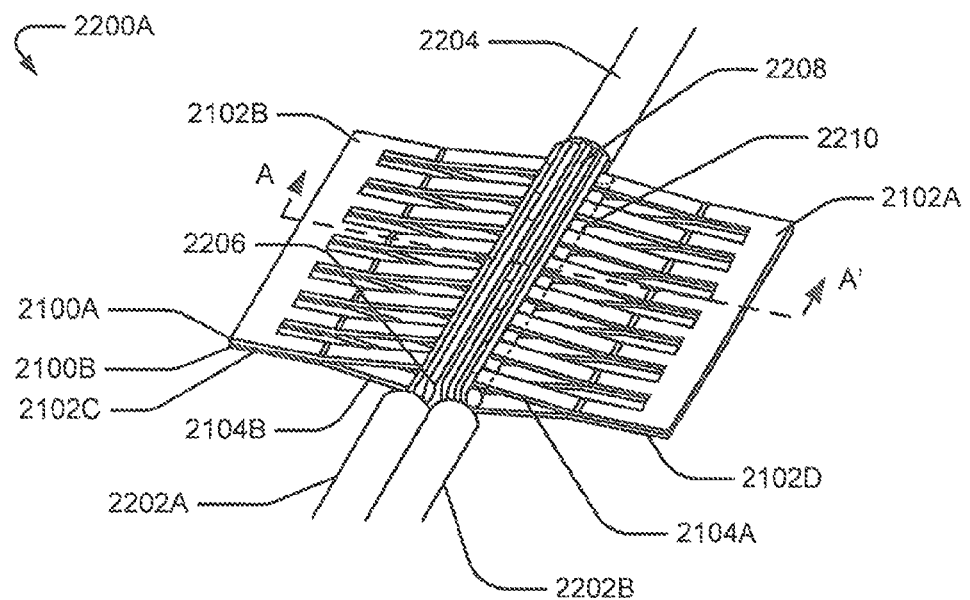
FIG. 22A is a schematic perspective view of one embodiment of a connected ladder pre-junction element with attached conductive wires from two proximal leads and one distal lead, according to the invention.

FIG. 22A is a perspective view of a connected pre junction element 2200A including multiple conductive wire connections to the combination of pre junction elements 2100A, 2100B. As shown, one or more conductive wires 2206 of each of proximal leads 2202A, 2202B may be connected or welded to the rungs or tabs 2104A, 2104B of the pre junction elements 2100A, 2100B, respectively. In other embodiments, there may be less than or more than two proximal leads 2202. Similarly, multiple conductive wires 2208 of distal lead 2204 are joined or welded to the tabs 2104A, 2104B.

Figure 22B:
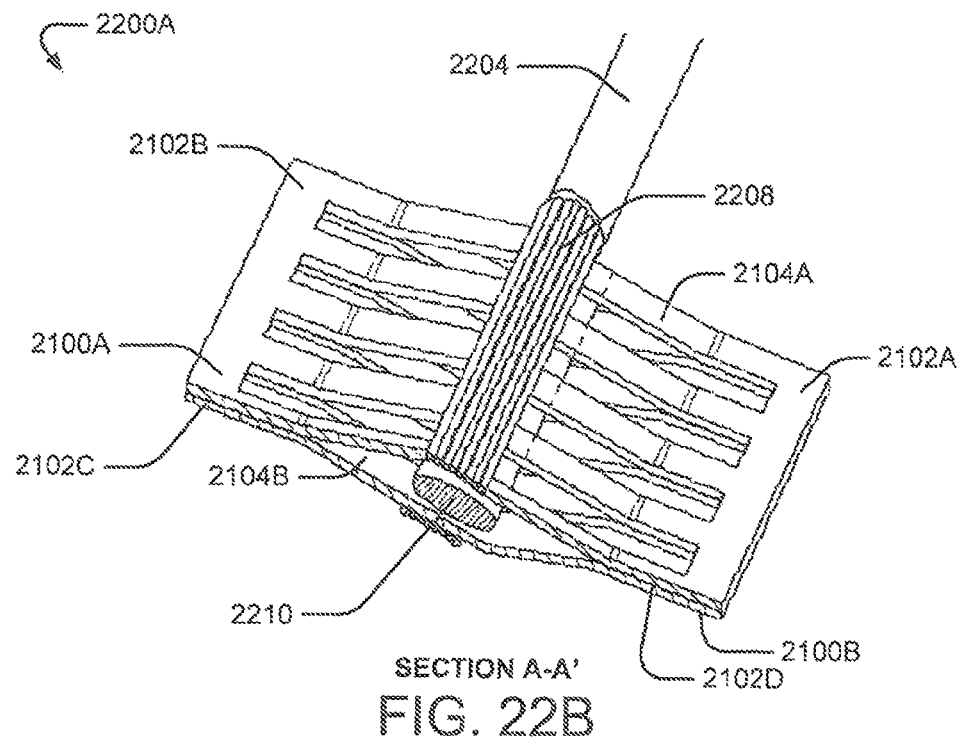
FIG. 22B is a schematic cross-sectional view of the connected metal ladder pre junction element of the FIG. 22A, according to the invention.

FIG. 22B is a cross-sectional view of the connected pre junction element of FIG. 22A. After all the conductive wire connections have been welded to either of the two pre junction elements 2100A, 2100B, the pre junction elements 2100A and 2100B form a sandwich around a piece of nonconductive tubing 2210, with a central lumen for stylet passage.

Figure 23:
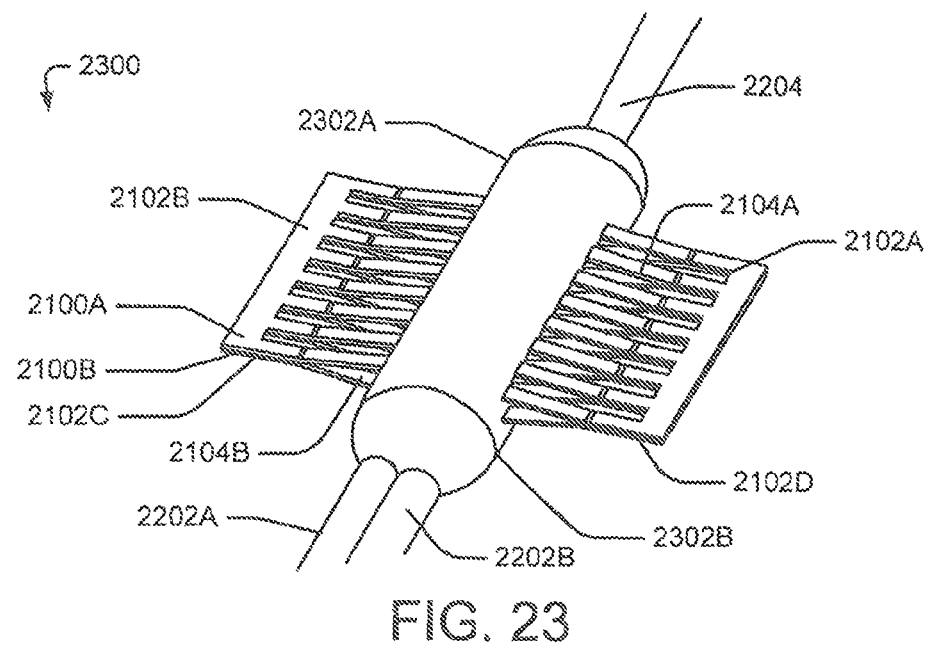
FIG. 23 is a schematic perspective view of one embodiment of a partially encased ladder pre junction element, according to the invention.

The connected pre junction element 2200A is then placed in a first mold and packaged in a non-conductive material such as Hysol® epoxy or a similar medical grade epoxy, silicone, polyurethane, or any other suitable material. FIG. 23 shows an encased pre junction element 2300 after the first molding stage. In this embodiment, during the first molding stage, at least two half insulating capsules i.e. 2302A and 2302B are used to encase the connected pre junction element 2200A. At least a portion of each of the tabs 2104A-2104B is within the first mold after the first molding stage and may not be visible.

Figure 24A:
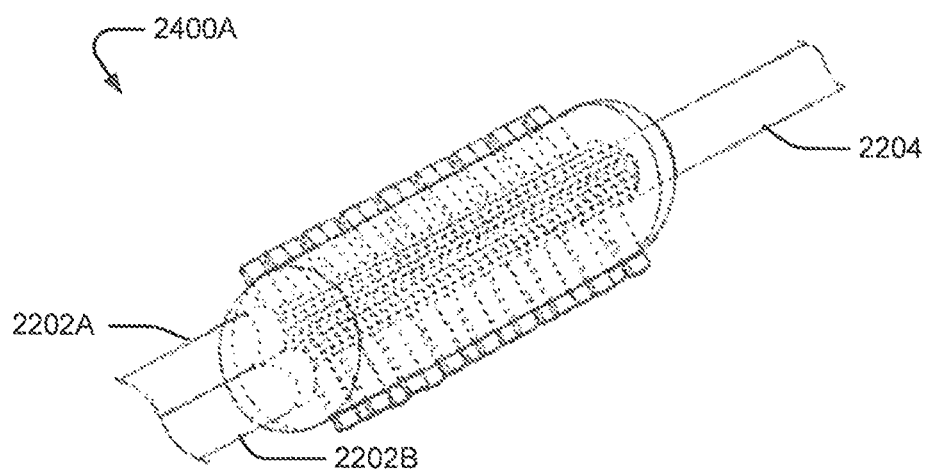
FIG. 24A is a schematic perspective view of one embodiment of a connected junction formed by removing runners from the partially encased metal ladder pre junction element of FIG. 23, according to the invention.

In the next step, the exposed parts of the pre junction element 2200A including the runners 2102A, 2102B, and 2102C, 2102D of the pre junction elements 2100A, 2100B, respectively, are removed from the encased pre junction element 2300. FIG. 24A illustrates a junction 2400A formed after removing runners 2102A-2102D from the encased pre junction element 2300. The exposed parts may be removed by using any suitable method such as, but are not limited to, cutting, grinding, and so forth. Removal of the runners 2102A, 2102B, 2102C, and 2102D results in electrical isolation of the individual conductive wires 2206 and 2208 from each other to define separate proximal conductive wires 2206 electrically connected to corresponding distal conductive wires 2208. The internal elements i.e. the tabs 2104 connected to the conductive wires 2206 and 2208 are shown with dotted lines and they may not be visible after the first molding stage.

Figure 24B:
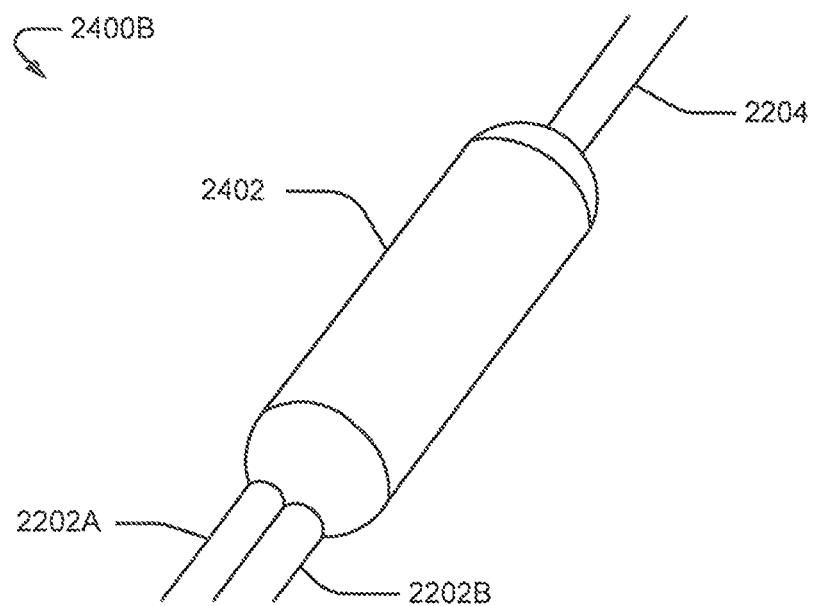
FIG. 24B is a schematic perspective view of one embodiment of a coupled lead arrangement formed using the ladder pre junction element of FIG. 21B, according to the invention.

Thereafter, a touch up operation or a second molding stage may cover the exposed tips of the tabs 2104A, 2104B. The junction 2400A is encased in a second capsule 2402 in a second molding stage to cover the exposed tips or portions of the ladder tabs 2104A, 2104B. FIG. 24B depicts a coupled lead arrangement 2400B after the second molding stage. The second or outer capsule 2402 isolates the tabs 2104A, 2104B completely from the outer environment.

Figure 25:
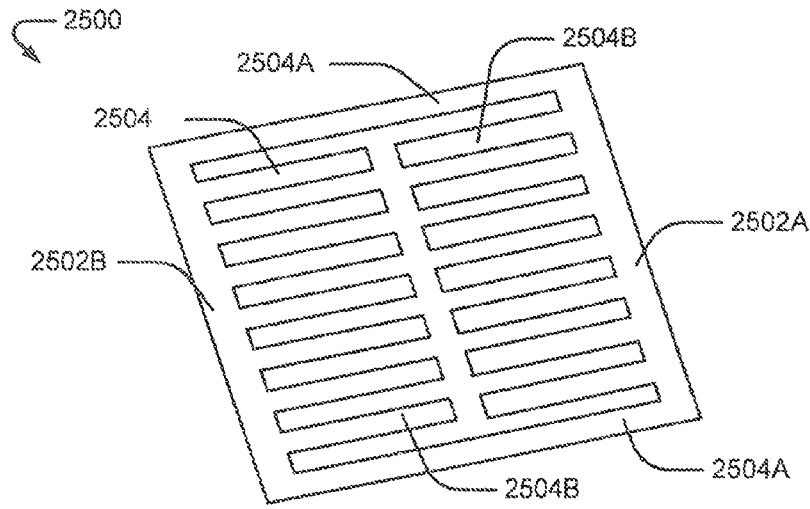
FIG. 25 is a schematic top view of one embodiment of a broken ladder pre junction element, according to the invention.

FIG. 25 illustrates one embodiment of a broken ladder pre junction element 2500. The broken ladder pre junction element 2500 includes a number of tabs 2504 that may act as weld points by connecting a number of leads to the broken ladder pre junction element 2500. The rungs of the ladder junction 2500 are the tabs 2504 to which conductive wires of one or more cables may be welded. The broken ladder pre junction element 2500 further includes at least two runners 2502A, 2502B extending along the sides of the tabs 2504. The runners 2502A, 2502B may connect the tabs 2504 to each other. The broken ladder pre junction element 2500 has nine rungs. The broken ladder pre junction element 2500 has seven tabs 2504B broken in the middle providing fourteen weld points for conductive wire pairs. The unbroken rungs 2504A (e.g., a proximal tab and a distal tab of the tabs 2504 as illustrated in FIG. 25) each serve as a weld point. Therefore, in the illustrated embodiment, the broken ladder pre junction element includes sixteen tabs 2504. The broken ladder pre junction element 2500 may be formed by stamping, etching, laser cutting, or using any suitable process. It will be understood that the number of total tabs, the number of unbroken tabs, and the number of broken tabs can be varied to provide different embodiments of a broken ladder pre junction element.

Figure 26:
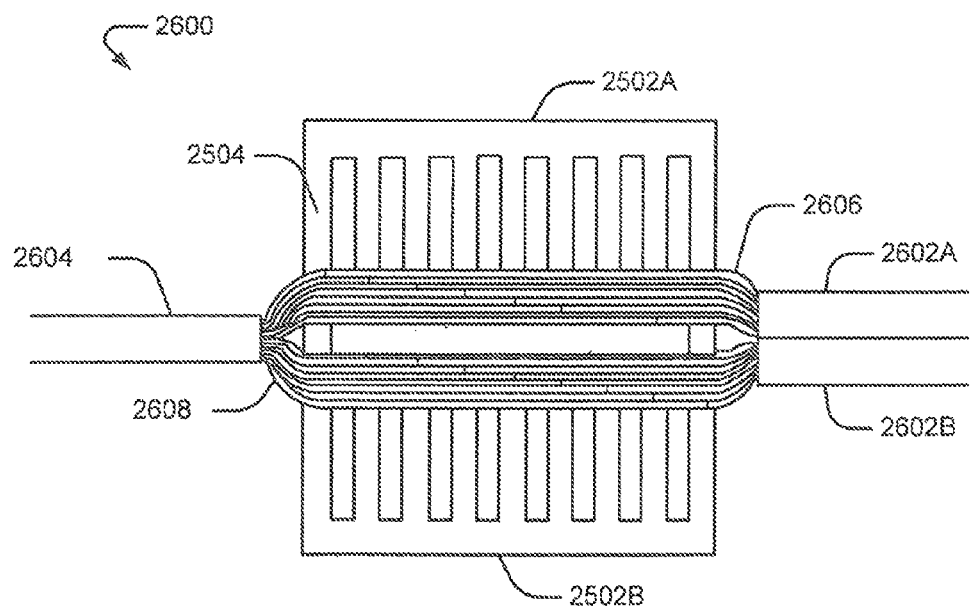
FIG. 26 is a schematic top view of one embodiment of a connected broken ladder pre-junction element with attached conductive wires from two proximal leads and one distal lead, according to the invention.

FIG. 26 depicts a connected pre junction element 2600 with conductive wires 2606 of proximal leads 2602A, 2602B and conductive wires 2608 of distal lead 2604 are connected to the tabs 2504. The conductive wires 2606-2608 may be connected to the tabs 2504 by using any suitable attachment method such as, for example, welding, brazing, and the like. As in the previous embodiments, more or fewer proximal and distal leads may be connected to the pre-junction element 2600.

Figure 27:
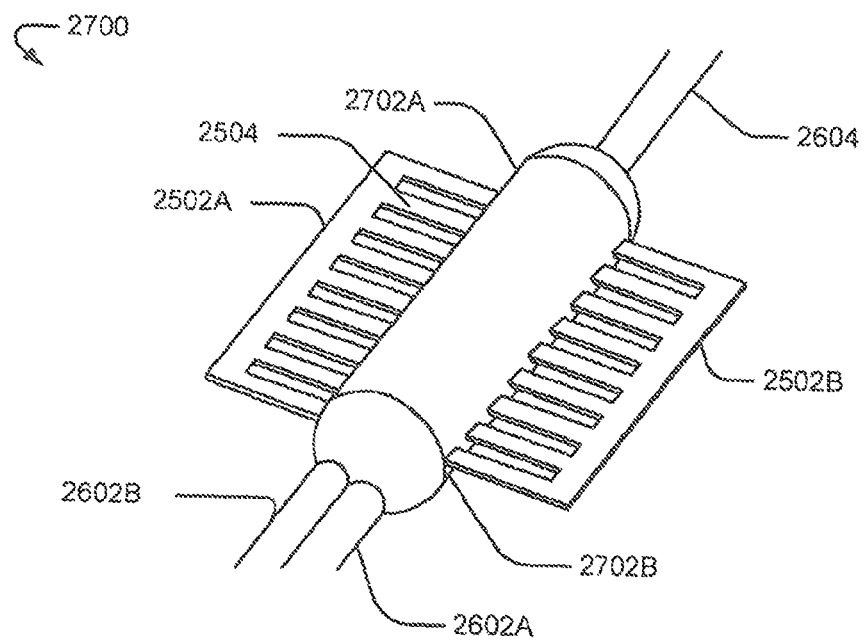
FIG. 27 is a schematic perspective view of one embodiment of a partially encased broken ladder pre junction element, according to the invention.

After connecting the distal conductive wires 2608 and the proximal conductive wires 2606, the pre junction element and the tabs may be packaged within a polymer casing. FIG. 27 depicts an encased pre junction element 2700 after a first molding stage. In the first molding stage, the connected pre junction element 2600 is molded in at least one insulating capsule 2702 using an insulating material to form an encased pre junction element 2700. In an embodiment, the connected pre junction element 2600 is molded in at least two insulating capsules 2702A-2702B. The insulating capsule 2702 is made up of a non-conductive material or insulating material such as Hysol® epoxy or a similar medical grade epoxy, silicone, polyurethane, or the like.

Figure 28A:
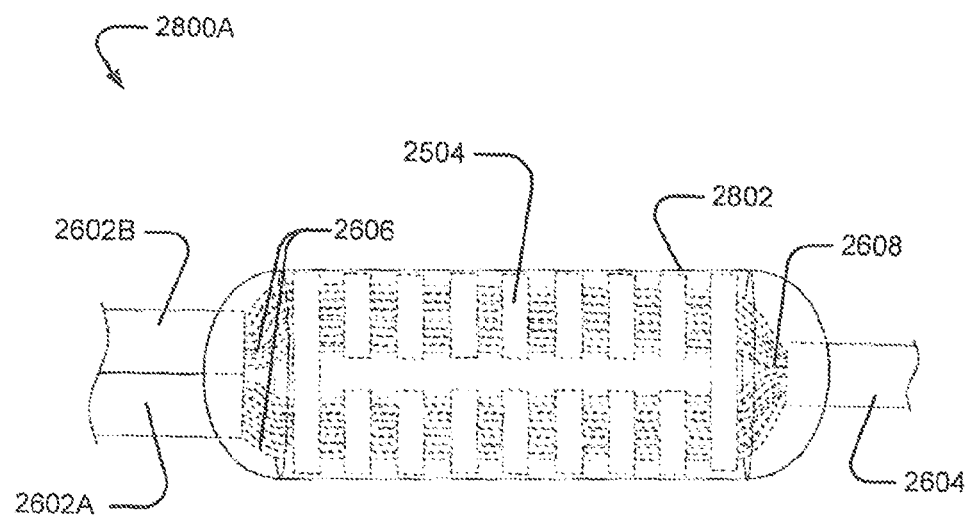
FIG. 28A is a schematic top view of one embodiment of a connected junction formed by removal of the runners from a broken ladder pre junction element, according to the invention.
Figure 28B:
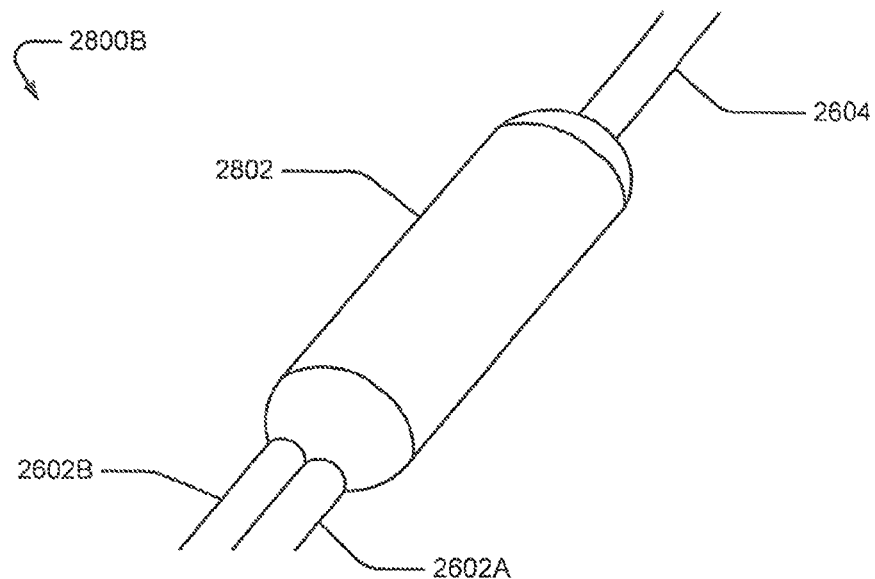
FIG. 28B is a schematic perspective view of a coupled lead arrangement formed using a broken ladder pre junction element, according to the invention.

The portion of the broken ladder pre junction element 2500 beyond the insulating capsule 2702, for example, the runners 2502A, 2502B and optionally portions of the tabs 2504 extending beyond the insulating capsule 2702, are cut off to electrically isolate each of the tabs 2504. FIG. 28A illustrates a connected junction 2800A after removal of the runners 2502A, 2502B. After cutting the runners 2502A, 2502B, the connected junction 2800A without the runners 2502A, 2502B is encased in a second insulating capsule 2802 to cover exposed tips of each of the metal tabs 2504 in a second molding stage. The exposed tips of the tabs 2504 are isolated by a touch-up operation or by the second molding stage. FIG. 28B depicts a coupled lead arrangement 2800B after second molding stage that is formed by using a broken ladder pre junction element 2500.

Figure 29:
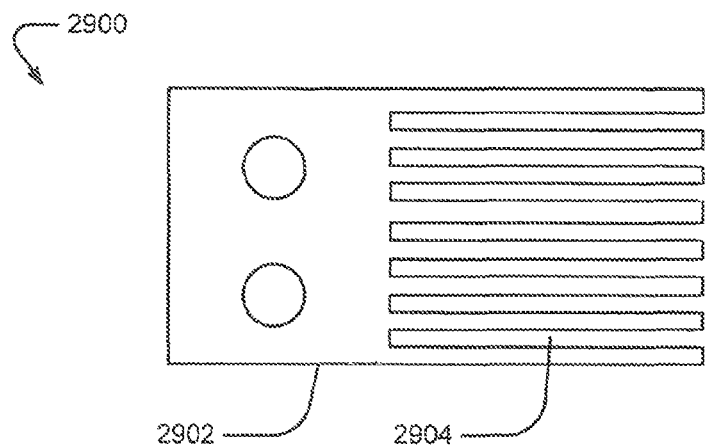
FIG. 29 is a schematic top view of one embodiment of a half-ladder pre junction element, according to the invention.

FIG. 29 illustrates one embodiment of another type of pre junction element: a flat (or skewed) half-ladder pre junction element 2900. To construct a sixteen channel system or coupled lead arrangement at least two half-ladder pre junction elements 2900A, 2900B may be used, as shown, for example, in FIG. 30. The half-ladder pre junction elements 2900A, 2900B each include a number of tabs. In addition, each of these pre junction elements 2900A, 2900B includes a runner 2902A, 2902B respectively. Each of the runners 2902A, 2902B optionally has at least one or more holes to facilitate fixation during one or more steps in the manufacturing process (e.g., welding of conductive wires, encapsulation, or the like). The pre junction elements 2900A, 2900B may be produced or formed via etching, stamping, laser cutting, or other suitable processes.

The tabs 2904 may be connected to conductive wires (not shown) of proximal leads 3002A, 3002B and distal lead 3004 in a similar manner to the preceding embodiments. After connecting the conductive wires, the pre junction elements 2900A, 2900B are arranged in a coplanar (FIG. 30) or skewed (FIG. 31) arrangement for a first molding or casting stage.

Figure 30:
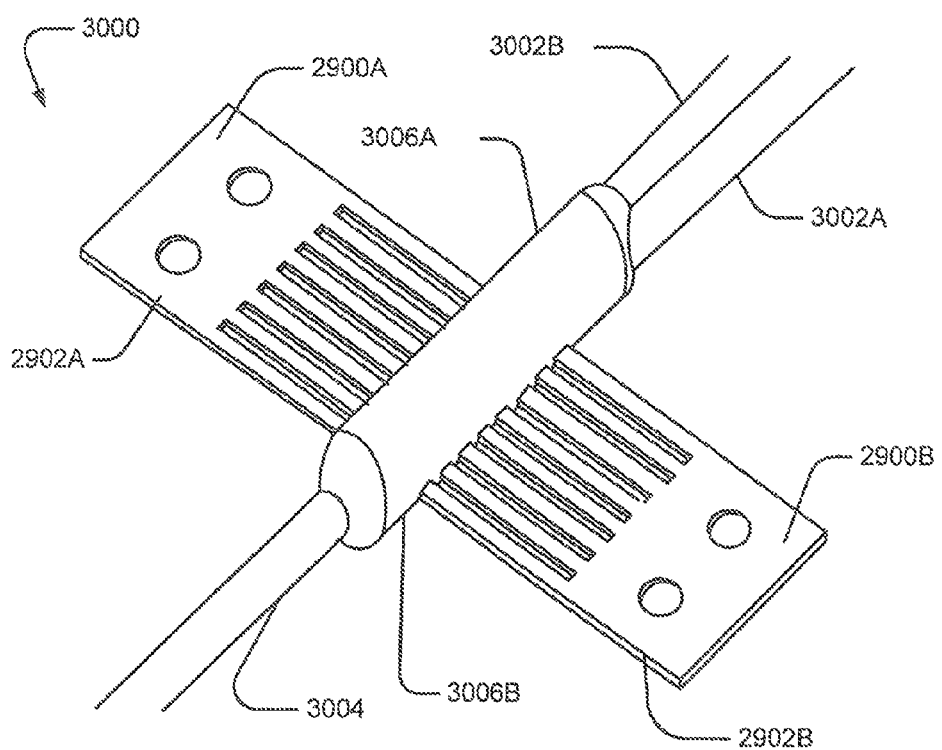
FIG. 30 is a schematic perspective view of one embodiment of a partially encased pre-junction element formed using two half-ladder pre junction elements, according to the invention.

After connecting the conductive wires of the proximal leads 3002, -3002B and the distal lead 3004 to the tabs 2904, the pre junction elements 2900A, 2900B are molded together to form a common encapsulated body 3006 as shown in FIG. 30. In one embodiment, the assembly having conductive wire connections and pre junction elements 2900A, 2900B is molded in, for example, at least two molded body sections 3006A, 3006B. The pre junction elements 2900A, 2900B may be held in position by pins (not shown) in the molding apparatus. The utilization of the skewed half-ladder pre junction elements 2900A, 2900B allows for a smoother transition from one to two lead bodies. In at least one embodiment, a polymer casing encases the welded section of the tabs. An assembly 3000 after the first molding stage is shown in FIG. 30. The sections of the half-ladder pre junction elements 2900A, 2900B that are outside the molded body section 3006 or the casing in the assembly 3000 are removed, electrically isolating the tabs.

Figure 31:
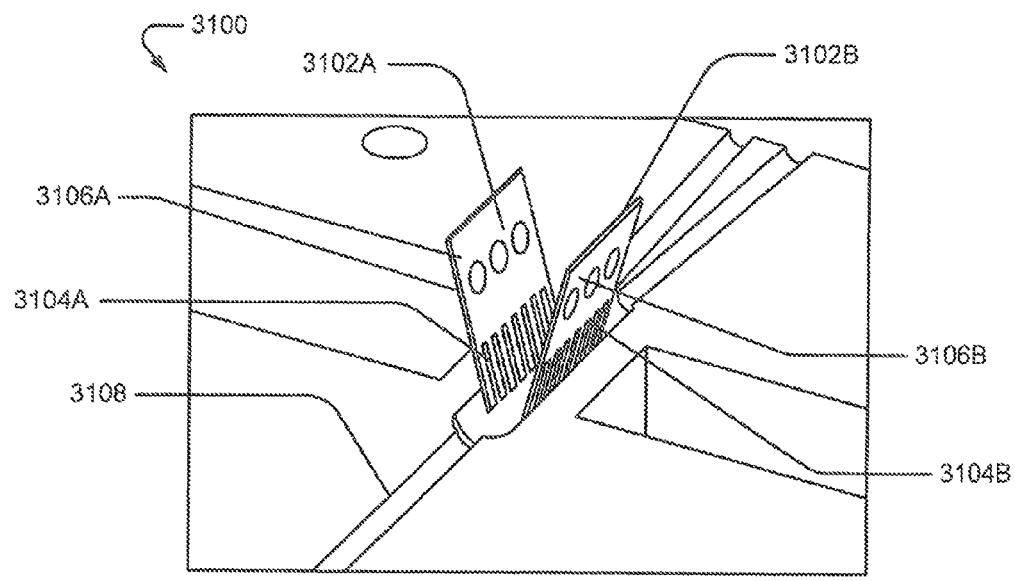
FIG. 31 is a schematic perspective view of one embodiment of an alternative placement of two half-ladder pre junction elements, according to the invention.

In at least some embodiments, the half-ladder pre junction elements 3102A, 3102B are placed at an angle different from 180° with respect to each other as shown in FIG. 31. The angle between the half-ladder pre junction elements 3102A, 3102B can be, for example, in the range of 20° to 160°, 30° to 150°, 40° to 140°, 50° to 130°, 60° to 120°, 70° to 110°, or 80° to 100°, or any other suitable angle. In such embodiments, the two pre junction elements 3102A, 3102B are positioned so that the ends of the tabs 3104A, 3104B are within the bath portion of the bottom half of a molding apparatus 3100. The tabs 3104A, 3104B are connected to each other through runners 3106A and 3106B respectively. The molding apparatus 3100 may be designed so that the pre junction elements 3102A, 3102B may be held at a desired angle to the horizontal. The leads may be placed in one or more grooves 3108 while connecting the conductive wires to the tabs 3104 or while molding around portions of the pre junction elements 3102A, 3102B.

Figure 32:
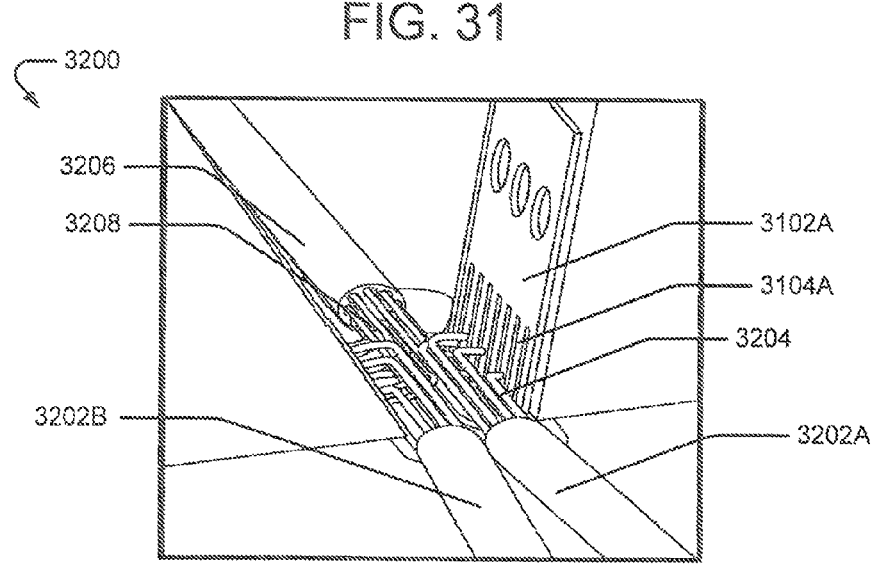
FIG. 32 is a schematic perspective view of one embodiment of the pre junction elements of FIG. 31 with conductive wires from two proximal leads and one distal lead attached, according to the invention.
Figure 33:
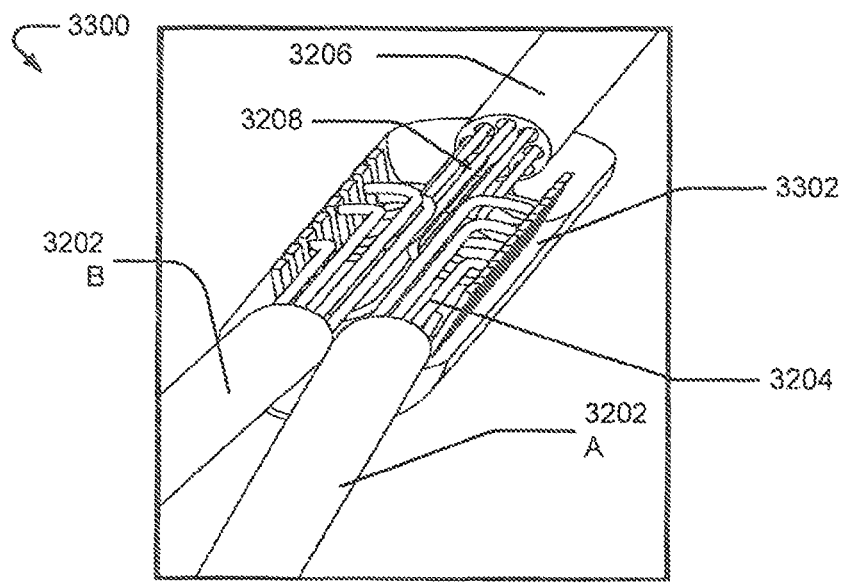
FIG. 33 is a schematic perspective view of the embodiment of FIG. 32 after partially encased and runner are removed from half-ladder pre junction elements, according to the invention.

FIG. 32 illustrates a connected arrangement 3200 formed by placing the two half-ladder pre junction elements 3102A, 3102B at a desired angle. One or more conductive wires 3204 of at least two proximal leads 3202A, 3202B may be connected to the tabs 3104. Similarly, multiple conductive wires 3208 of a distal lead 3206 may be connected to the tabs 3104. In this embodiment, each of the proximal leads 3202A, 3202B have eight conductive wires 3204 and the distal lead 3206 have sixteen conductive wires 3208. The conductive wires 3204 and 3208 may be connected through any suitable attachment process, such as, but not limited to, a welding or brazing process. The conductive wires 3204, 3208 can be attached to the tabs 3104 prior to, or after, insertion in the mold. Connections or welds are positioned at the ends of the tabs 3104 so that the connections or welds may be encased in Hysol® epoxy or a similar medical grade epoxy, silicone, polyurethane, or any other suitable material, as shown in FIG. 33. After the open-faced molding or first molding step, the runners 3106A, 3106B connecting the tabs 3104A, 3104B can be removed from the half-ladder pre junction elements 3102A, 3102B to electrically isolate the tabs 3104. FIG. 33 shows a connected assembly 3300 after a first molding step, the exposed portions and the runners 3106A-3106B of the half-ladder pre junction elements 3102A-3102B are removed.

Figure 34:
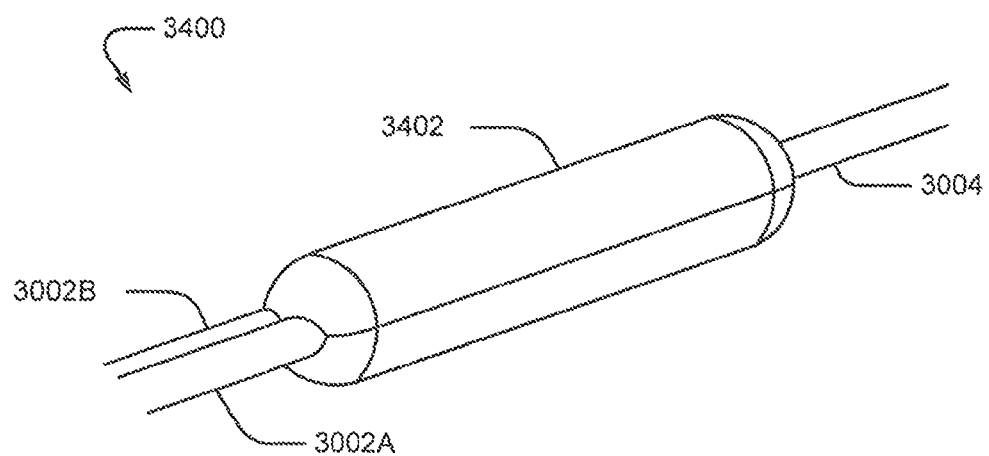
FIG. 34 is a schematic perspective view of a coupled lead arrangement formed using a two half-ladder pre junction element, according to the invention.

Thereafter, in a second molding stage, the connected assembly 3300 is encased in a second encapsulation capsule 3402 as shown in FIG. 34. FIG. 34 shows a coupled lead arrangement 3400 formed after the second molding stage, in accordance with an embodiment of the present disclosure. The second encapsulation capsule 3402 may be made up of a non-conductive material or an insulating material such as Hysol® epoxy or a similar medical grade epoxy, silicone, polyurethane, or any other suitable material, to physically and electrically isolate the exposed parts of the tabs 3104A, 3104B.

Figure 35:
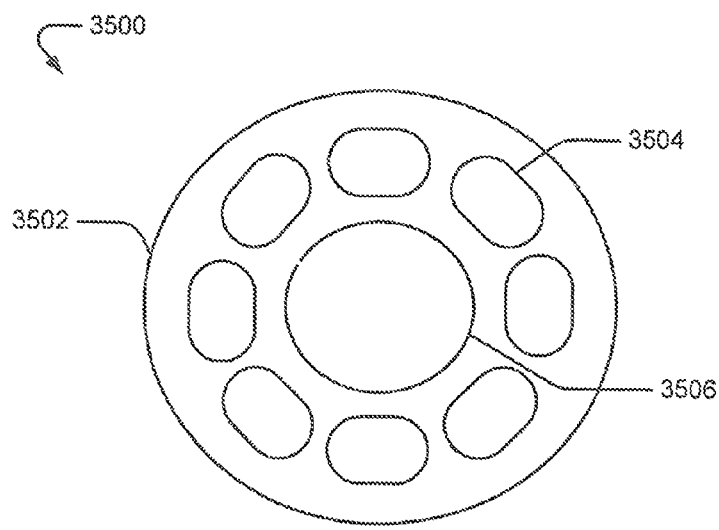
FIG. 35 is a schematic top view of one embodiment of a contact element, according to the invention.

FIG. 35 illustrates an embodiment of one of a series of contact elements 3500 that form another type of junction element. The contact element 3500 includes a cylindrical conductive body 3502 defining one or more peripheral lumens 3504 and one central lumen 3506. In the illustrated embodiment, the cylindrical body 3502 contains eight peripheral lumens 3504. Thus, eight conductive wires can be disposed individually through one of the eight peripheral lumens 3504. In alternate embodiments, the peripheral lumens 3504 can be configured and arranged to each accommodate more than one conductive wire. FIG. 35 shows only eight peripheral lumens 3504, but other embodiments can include any number of peripheral lumens 3504. In addition, one or more conductive wires may pass through the central lumen 3506.

Each contact element 3500 acts analogously to a tab in the preceding embodiments to electrically connect, for example, one wire from a proximal lead to one wire from a distal lead. The contact element 3500 may be produced via, for example, stamping, laser cutting, or any other suitable process. A number of contact elements 3500 may be used to form a coupled lead arrangement. In one embodiment, four or eight contact elements may be used to form a coupled lead arrangement.

Figure 36:
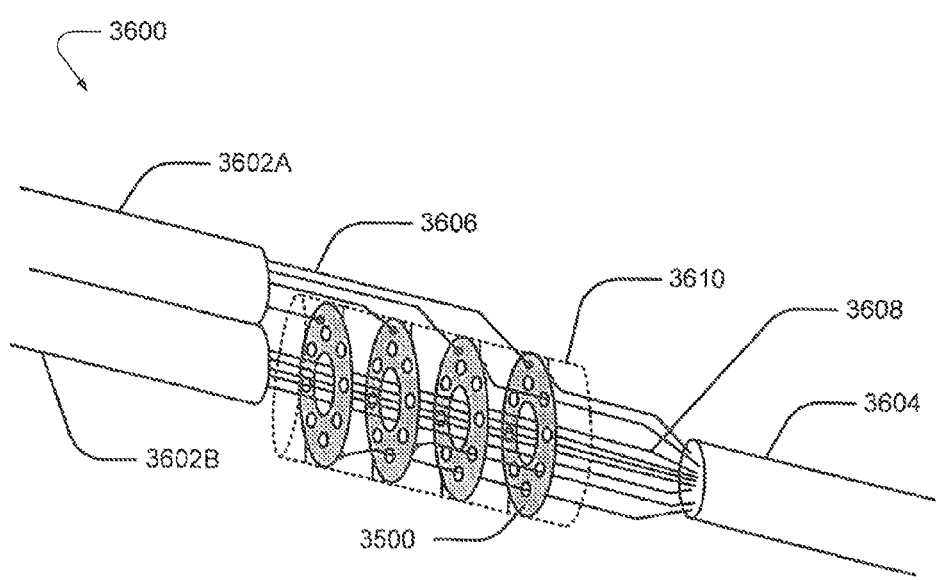
FIG. 36 is a schematic perspective view of a series of contact elements disposed between two proximal leads and a distal lead with some conductive wires from the leads attached to the contact elements, according to the invention.

FIG. 36 illustrates an exemplary connected assembly 3600 formed using four contact elements 3500. It will be recognized that any number of contact elements can be used including, for example, eight contact elements. As shown, the connected junction 3600 in this embodiment includes conductive wires of two proximal leads 3602A, 3602B and a distal lead 3604. In this embodiment, each of the proximal leads 3602A, 3602B includes four conductive wires 3606 and the distal lead 3604 includes eight conductive wires 3608.

The conductive wires from proximal lead 3602B pass through the central lumen 3506 (FIG. 35) of each of the contact elements 3500 and proceed as conductive wires 3608 of distal lead 3604. The conductive wires of proximal lead 3602A are each attached to a different one of the contact elements 3500. The corresponding conductive wires 3608 from the distal lead 3604 are also each attached to a different one of the contact elements 3500, passing through a peripheral lumen 3504 (FIG. 35) of each preceding contact element 3500. Attachment of the conductive wires 3606, 3608 to the contact elements can be performed using welding, brazing, or any other suitable attachment process.

Figure 37:
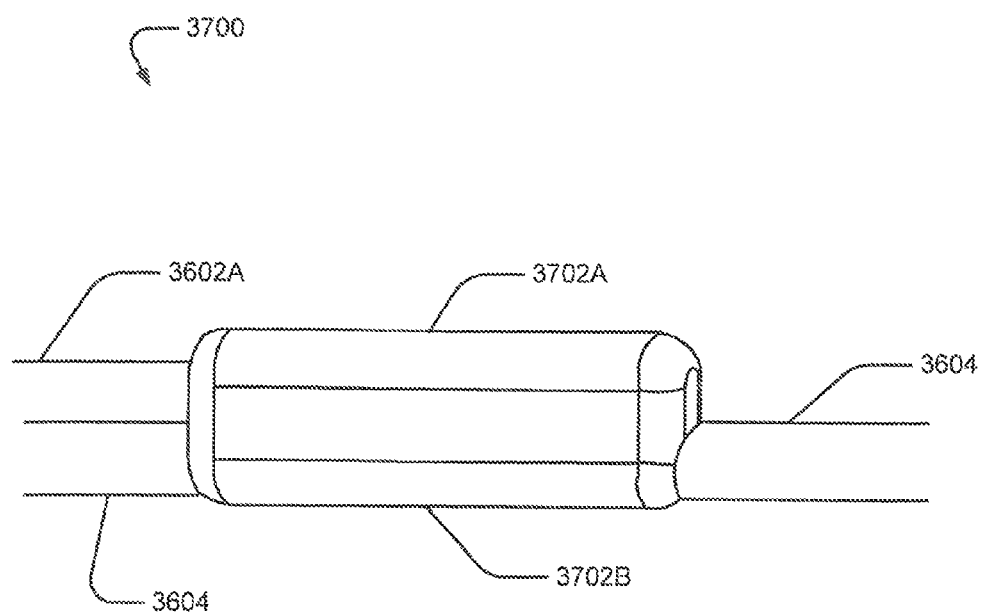
FIG. 37 is a schematic side view of one embodiment of a coupled lead arrangement formed using contact elements, according to the invention.

In at least one embodiment, the contact elements 3500 may be held together using a support member 3610. The support member 3610 may be a plastic tube, a molded structure, or the like. The connected assembly 3600 may be molded in at least one mold to define an encapsulation 3702 as shown in FIG. 37. The coupled lead arrangement 3700 in this embodiment is formed from embedded contact elements 3500. In one embodiment, the connected assembly may be molded in two parts 3702A and 3702B. The encapsulation 3702 is made up of a non-conductive material to physically and electrically isolate the contact elements 3500.

Embodiments of the present disclosure may be used in any medical or non-medical procedure, including any medical procedure where one or more body part requires electrical stimulation. In addition, at least certain aspects of the aforementioned embodiments may be combined with other aspects of the embodiments, or removed.

While the present disclosure has been described by means of specific embodiments and applications thereof, numerous modifications and variations could be made thereto by those skilled in the art without departing from the scope of the present disclosure set forth in the claims.

What is claimed is:

1. A lead arrangement, comprising:
    a plurality of proximal leads, each proximal lead having a proximal end and a distal end and comprising a plurality of conductive contacts disposed along the proximal end and a plurality of conductive wires coupled to the conductive contacts and extending to the distal end of the proximal lead;
    at least one distal lead, each distal lead having a proximal end and a distal end and comprising a plurality of electrodes disposed along the distal end and a plurality of conductive wires coupled to the electrodes and extending to the proximal end of the distal lead; and
    a junction electrically and mechanically coupling the plurality of proximal leads to the at least one distal lead, the junction comprising a plurality of conductive tabs and a non-conductive material encapsulating the plurality of conductive tabs, wherein ends of the conductive wires of the at least one distal lead and ends of the conductive wires of the plurality of proximal leads are directly welded, soldered, or brazed to the plurality of conductive tabs of the junction.

2. The lead arrangement of claim 1, wherein the plurality of conductive tabs are separated from each other by the non-conductive material encapsulating the plurality of conductive tabs.

3. The lead arrangement of claim 2, wherein the non-conductive material comprises medical grade epoxy.

4. A method of making the coupled lead arrangement of claim 1, the method comprising:
    providing a pre-junction element comprising the plurality of conductive tabs extending from at least one runner;
    directly welding, soldering, or brazing exposed ends of the plurality of conductive wires from the plurality of proximal leads and from the at least one distal lead to the conductive tabs o the pre-junction element to form a connected pre-junction element, wherein, for each of the conductive tabs to which a one of the conductive wires from the at least one distal lead is welded, soldered, or brazed, at least one of the conductive wires from at least one of the plurality of proximal leads is also welded, soldered, or brazed;
    partially encasing the connected pre-junction element in a first non-conductive material;
    removing the at least one runner to electrically isolate the conductive tabs from each other and to form a connected junction; and
    encasing exposed portions of the connected junction in a second non-conductive material, wherein the first and second non-conductive material form the non-conductive material encapsulating the conductive tabs.

5. The method of claim 4, wherein the first non-conductive material is a same material as the second. non-conductive material.

6. The method of claim 4, wherein providing a pre-junction element comprises providing a pre-junction element formed from a rectangular tube, a square tube, or a hypo tube.

7. The method of claim 4, wherein providing a pre-junction element comprises providing a pre-junction element selected from a rounded rib cape pre-junction element, a square rib cage pre-junction element, or at least one ladder pre-junction element.

8. The method of claim 4, wherein the pre junction element is a broken ladder pre-junction element comprising a plurality of rungs with some of the rungs being broken to form two individual tabs and at least one of the rungs being unbroken to form a single tab extending from one side of the pre junction element to an opposing side of the pre junction element.

9. The method of claim 4, wherein the pre-junction element is two ladder pre-junction elements disposing opposing each other and each bent to form an arch.

10. The method of claim 9, further comprising providing a non-conductive tubing between the two ladder pre-junction elements.

11. The method of claim 4, wherein the pre junction element is two metal ladder pre-junction elements, the method further comprising positioning the two metal ladder pre-junction elements opposing each other for welding, soldering, or brazing of the exposed ends the plurality of conductive wires.

12. The method of claim 11, wherein positioning the two metal ladder pre-junction elements comprises positioning the two metal ladder pre-junction elements at an angle of less than 180° with respect to each other.

13. The method of claim 4, wherein the pre-junction element is a single flat ladder pre-junction element.

14. The method of claim 4, wherein the first and second non-conductive materials comprise medical grade epoxy.

15. A lead arrangement, comprising:
a plurality of proximal leads, each proximal lead having a proximal end and a distal end and comprising a plurality of conductive contacts disposed along the proximal end and a. plurality of conductive wires coupled to the conductive contacts and extending to the distal end of the proximal lead;
at least one distal lead, each distal lead having a proximal end and a distal end and comprising a plurality of electrodes disposed along the distal end and a plurality of conductive wires coupled to the electrodes and extending to the proximal end of the distal lead; and
a junction disposed between the plurality of proximal leads and the at least one distal lead, the junction comprising a series of contact elements disposed sequentially between the plurality of proximal leads and the at least one distal lead and a non-conductive material encapsulating the contact elements, each of the contact elements defining a central lumen, wherein ends of at least some of the conductive wires of the at least one distal lead and ends of the conductive wires of at least one of the plurality of proximal leads are electrically coupled by welding, soldering, or brazing to the plurality of contact elements of the junction and wherein the conductive wires of at least one of the proximal leads pass through the central lumen of each of the contact elements and into the at least one distal lead to form some of the conductive wires of the at least one distal lead.

16. The lead arrangement of claim 15, wherein each of the contact elements defines a plurality of peripheral lumens disposed around the central lumen.

17. The lead arrangement of claim 16, wherein at least one of the conductive wires of the at least one distal lead passes through at least one of the peripheral lumens of at least one of the contact elements.

18. The lead arrangement of claim 17, wherein at least one of the conductive wires of the plurality of proximal leads passes through at least one of the peripheral lumens of at least one of the contact elements.

19. A method of making the lead arrangement of claim 15, the method comprising:
providing the series of contact elements disposed sequentially between the plurality of proximal leads and the at least one distal lead;
welding, soldering, or brazing exposed ends of the plurality of the conductive wires from at least one of the plurality of proximal leads and from the at least one distal lead to the contact elements to form a connected junction, wherein, for each of the contact elements to which a one of the conductive wires from the at least one distal lead is welded, soldered, or brazed, at least one of the conductive wires from the at least one of the plurality of proximal leads is also welded, soldered, or brazed;
passing a plurality of the conductive wires from at least one of the plurality of proximal leads through the central lumens of the contact elements and into the at least one distal lead to form some of the conductive wires of the at least one distal lead; and
encasing the connected junction in the non-conductive material.

20. The method of claim 19, wherein each of the contact elements defines a plurality of peripheral lumens disposed around the central lumen and wherein the method further comprises passing at least one of the conductive wires from at least one of the plurality of proximal ends through at least one of the peripheral lumens of at least one of the contact elements.

* * * * *